(12) United States Patent
Mu

(10) Patent No.: US 12,279,898 B2
(45) Date of Patent: Apr. 22, 2025

(54) SPREAD FIELD IMAGING COLLIMATORS FOR RADIATION-BASED IMAGING AND METHODS OF USING THE SAME

(71) Applicant: Argospect Technologies Inc., Foster City, CA (US)

(72) Inventor: Zhiping Mu, Foster City, CA (US)

(73) Assignee: ARGOSPECT TECHNOLOGIES INC., Foster City, CA (US)

( * ) Notice: Subject to any disclaimer, the term of this patent is extended or adjusted under 35 U.S.C. 154(b) by 0 days.

(21) Appl. No.: 18/449,189

(22) Filed: Aug. 14, 2023

(65) Prior Publication Data

US 2023/0389882 A1 Dec. 7, 2023

Related U.S. Application Data

(62) Division of application No. 17/399,768, filed on Aug. 11, 2021, now Pat. No. 11,723,609.

(Continued)

(51) Int. Cl.
*A61B 6/06* (2006.01)
*A61B 6/42* (2024.01)

(52) U.S. Cl.
CPC .............. *A61B 6/06* (2013.01); *A61B 6/4266* (2013.01); *A61B 6/4291* (2013.01)

(58) Field of Classification Search
CPC ........ A61B 6/06; A61B 6/4266; A61B 6/4291
See application file for complete search history.

(56) References Cited

U.S. PATENT DOCUMENTS

| 4,165,462 A | * | 8/1979 | Macovski | ............... G01T 1/295 |
| | | | | 250/363.04 |
| 4,506,374 A | | 3/1985 | Flynn | |

(Continued)

FOREIGN PATENT DOCUMENTS

| JP | 2002328171 A | 11/2002 |
| JP | 2008537137 A | 9/2008 |

OTHER PUBLICATIONS

Charlotte Robert et al., Optimization of a parallel hole collimator/ CdZnTe gamma-camera architecture for scintimammography, Medical Physics, vol. 38, No. 4, Apr. 2011, pp. 1806-1819.

(Continued)

*Primary Examiner* — Blake C Riddick
(74) *Attorney, Agent, or Firm* — HAYNES AND BOONE, LLP

(57) ABSTRACT

A method includes obtaining an image having M sections and each section having N pixels. The method further includes deriving N sub-images from the image, wherein each sub-image has M sections and each section has N pixels. The i-th pixel of the j-th section of the i-th sub-image has a pixel value equal to a pixel value of the i-th pixel of the j-th section of the image and other pixels of the j-th section of the i-th sub-image are set to 0, where i traverses from 1 to N, and j traverses from 1 to M. The method further includes providing N projection patterns and calculating a projection for each sub-image by performing convolution of the respective sub-image with a corresponding one of the projection patterns, thereby obtaining N projected sub-images. The method further includes summing up the N projected sub-images, thereby obtaining a projection of the image.

13 Claims, 16 Drawing Sheets

Related U.S. Application Data

(60) Provisional application No. 63/168,778, filed on Mar. 31, 2021, provisional application No. 63/071,540, filed on Aug. 28, 2020.

(56) References Cited

U.S. PATENT DOCUMENTS

| | | |
|---|---|---|
| 6,271,524 B1 | 8/2001 | Wainer et al. |
| 6,353,227 B1 | 3/2002 | Boxen |
| 6,392,235 B1 | 5/2002 | Barrett et al. |
| 6,580,939 B1 | 6/2003 | Chaney et al. |
| 6,737,652 B2 | 5/2004 | Lanza et al. |
| 7,683,333 B2 | 3/2010 | Wieczorek |
| 7,692,156 B1 | 4/2010 | Nagarkar |
| 7,759,625 B2 | 7/2010 | Frangioni et al. |
| 8,237,124 B2 | 8/2012 | Marwala et al. |
| 9,349,495 B2 | 5/2016 | Shahar et al. |
| 2002/0145114 A1 | 10/2002 | Inoue |
| 2002/0159566 A1 | 10/2002 | Popescu |
| 2003/0001098 A1 | 1/2003 | Stoddart |
| 2005/0084072 A1 | 4/2005 | Pinchot |
| 2006/0261278 A1 | 11/2006 | Accorsi |
| 2007/0064876 A1 | 3/2007 | Hoffman |
| 2008/0029705 A1 | 2/2008 | Tsuchiya et al. |
| 2008/0087829 A1 | 4/2008 | Hoppin et al. |
| 2008/0116386 A1* | 5/2008 | Wagenaar ............... G01T 1/249 250/370.09 |
| 2008/0128625 A1 | 6/2008 | Lamadie |
| 2008/0230707 A1 | 9/2008 | Idoine |
| 2008/0237482 A1* | 10/2008 | Shahar ............... G21K 1/025 378/150 |
| 2009/0022278 A1 | 1/2009 | Hugg et al. |
| 2009/0167922 A1* | 7/2009 | Perlman ............... H04N 23/10 348/340 |
| 2009/0304150 A1 | 12/2009 | Metzler et al. |
| 2009/0310747 A1* | 12/2009 | Hoctor ............... G03B 42/02 378/62 |
| 2010/0067758 A1* | 3/2010 | Casey ............... G06T 11/006 382/128 |
| 2012/0305812 A1 | 12/2012 | Bowen et al. |
| 2014/0077095 A1 | 3/2014 | Deprez et al. |
| 2014/0267818 A1 | 9/2014 | Perlman |
| 2015/0177392 A1 | 6/2015 | Hefetz et al. |
| 2015/0216488 A1 | 8/2015 | Funk |
| 2016/0166223 A1* | 6/2016 | Besson ............... A61B 6/4007 378/9 |
| 2016/0235382 A1* | 8/2016 | Besson ............... A61B 6/032 |
| 2019/0116326 A1* | 4/2019 | Perlman ............... H04N 25/61 |
| 2020/0146641 A1 | 5/2020 | Mu |
| 2020/0261034 A1 | 8/2020 | Mu |
| 2020/0265617 A1 | 8/2020 | Mu |

OTHER PUBLICATIONS

International Searching Authority, International Search Report and Written Opinion of the International Searching Authority, PCT/US2021/045770, Dec. 28, 2021, 13 pages.

* cited by examiner

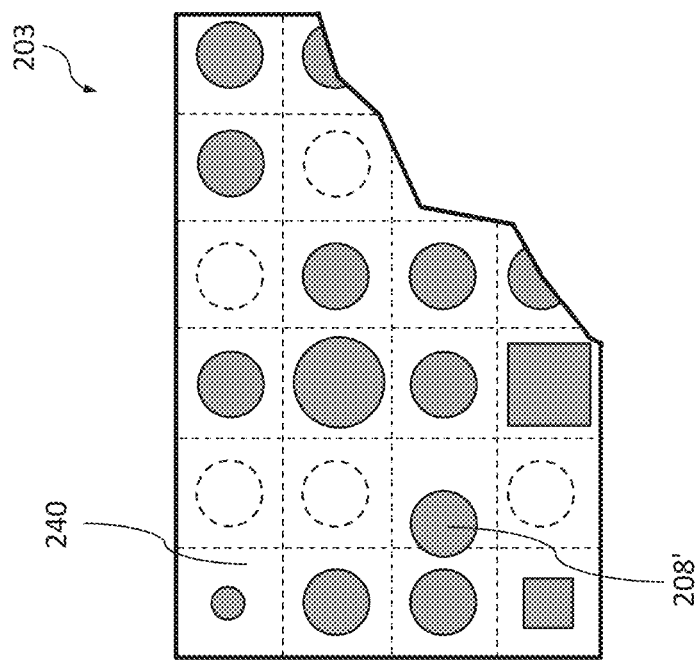
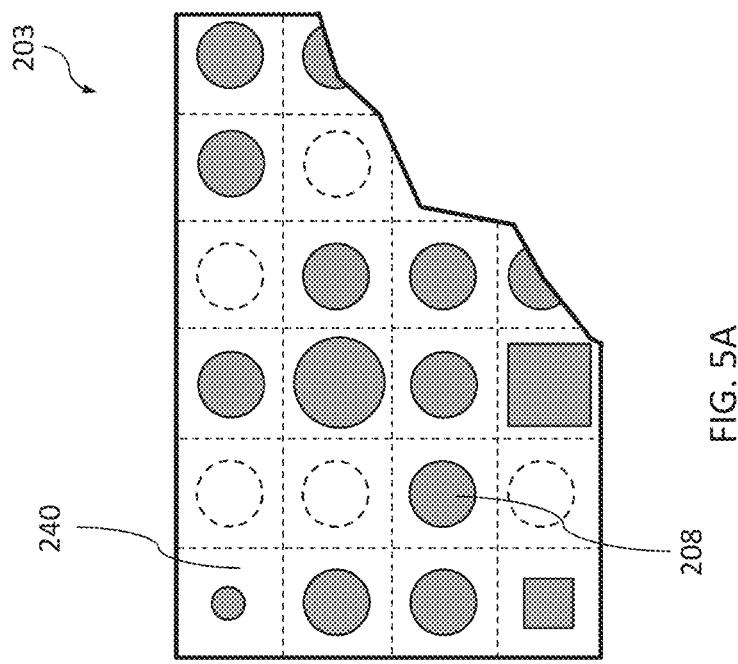

FIG. 7

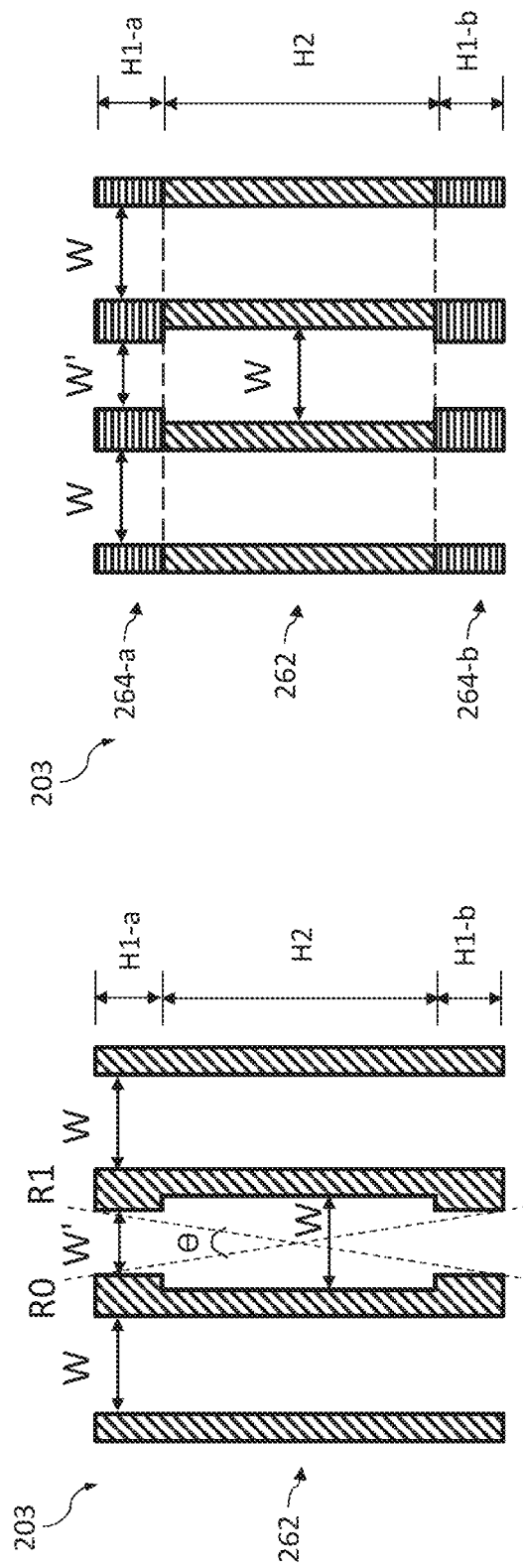
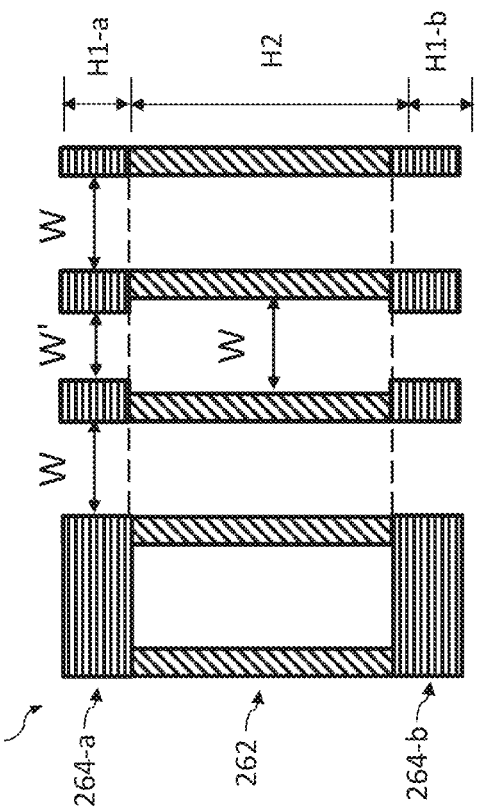
FIG. 9A
FIG. 9B
FIG. 9C

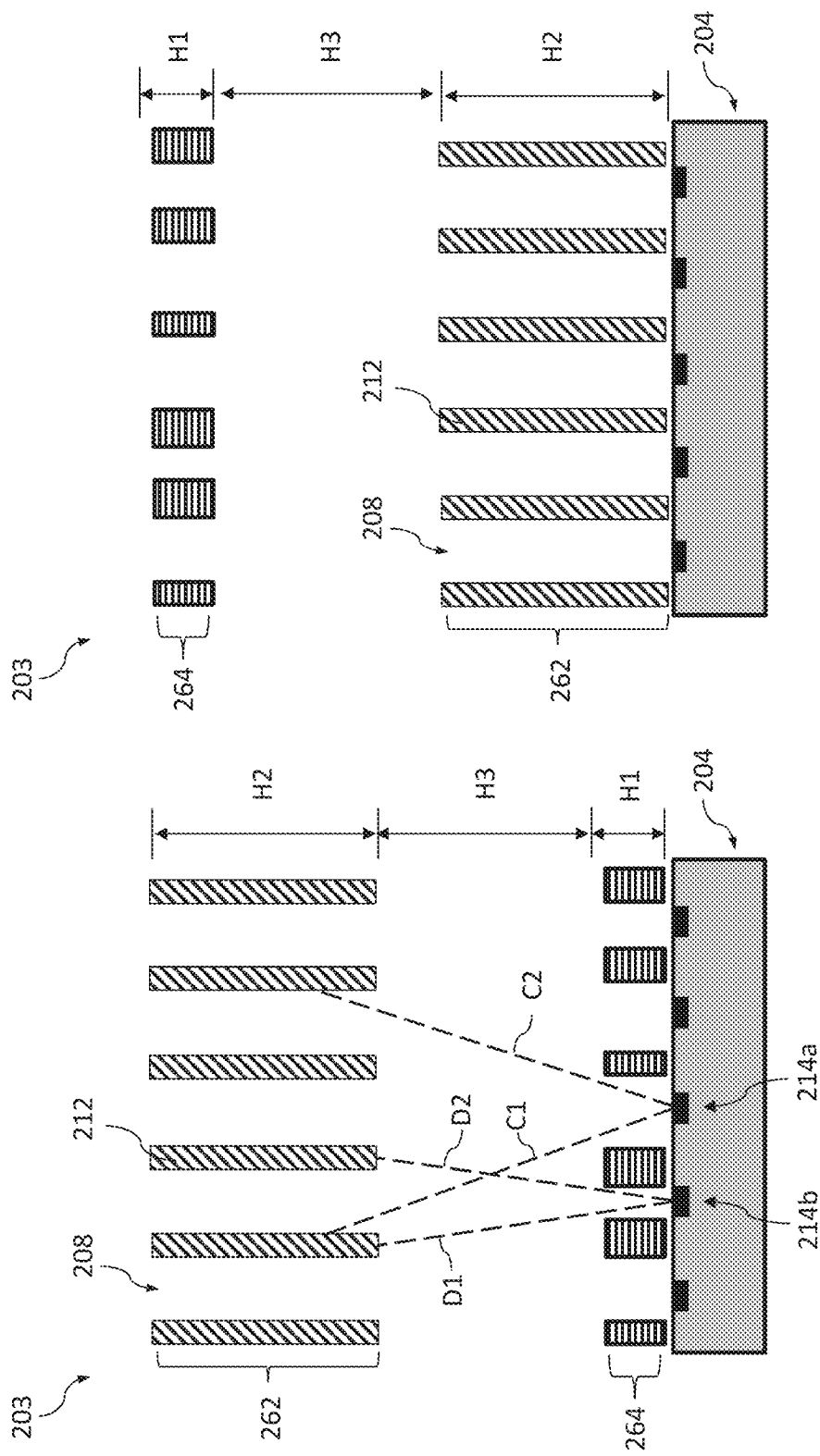

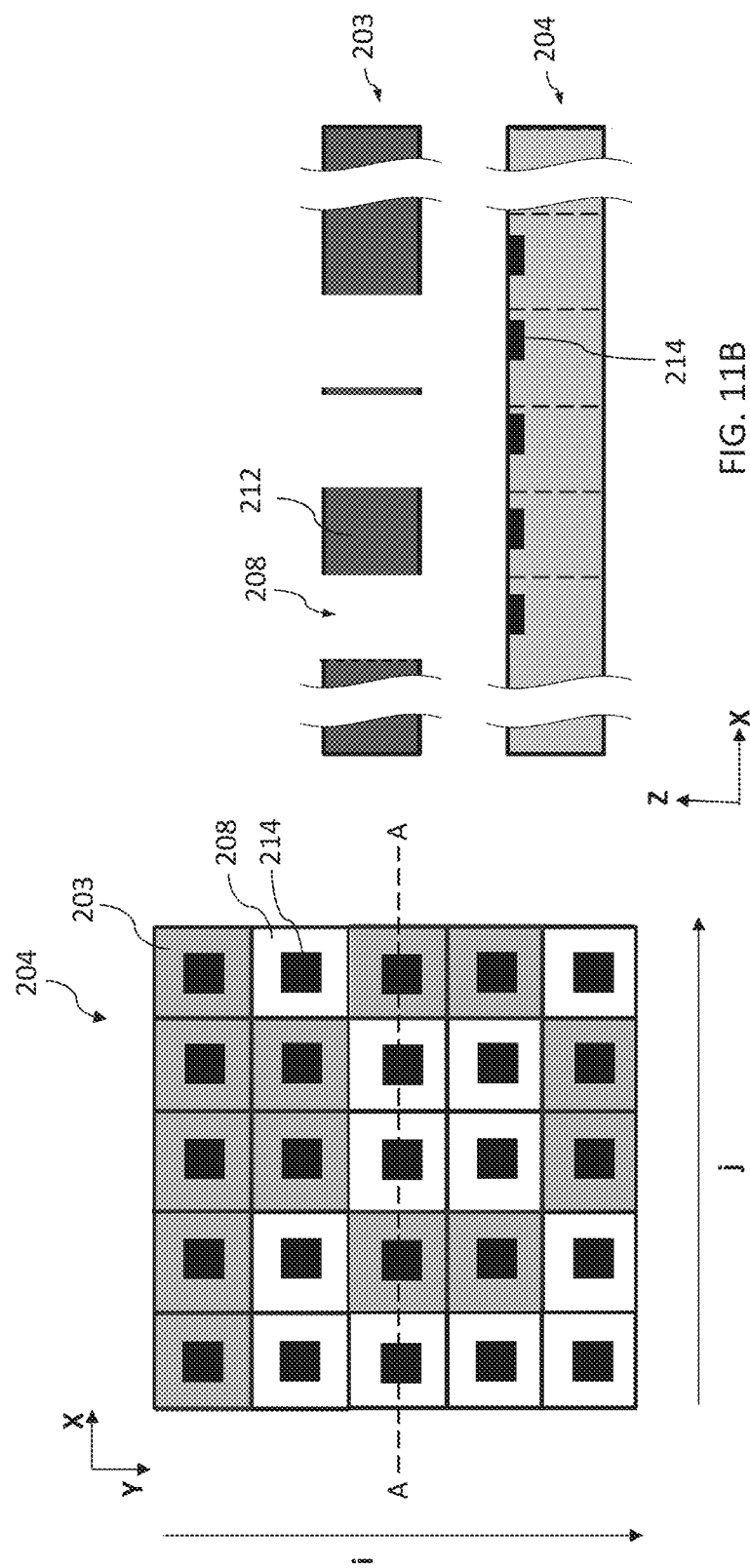

SPREAD FIELD IMAGING COLLIMATORS FOR RADIATION-BASED IMAGING AND METHODS OF USING THE SAME

PRIORITY

This is a divisional of U.S. application Ser. No. 17/399,768, filed Aug. 11, 2021, which claims the benefits of and priority to U.S. Provisional Application Ser. No. 63/168,778 filed Mar. 31, 2021 and U.S. Provisional Application Ser. No. 63/071,540 filed Aug. 28, 2020, the entire disclosure of which is herein incorporated by reference.

BACKGROUND

In radiation-based imaging, such as molecular medical imaging (sometimes known as nuclear medicine imaging), images representing radiopharmaceutical distributions may be generated for medical diagnosis. Prior to imaging, radiopharmaceuticals are injected into a target object such as a patient. The radiopharmaceuticals emit radioactive photons, which can penetrate through the body to be detected by a photon detector. Based on information from the received photons, the photon detector may then determine the distribution of the radiopharmaceuticals inside the patient. The distribution represents the physiological function of the patient, and therefore images of the distribution provide valuable clinical information for diagnosis of a variety of diseases and conditions such as those in cardiology, oncology, neurology, etc.

To generate images, collimator and photon detector work in tandem. A collimator is a device that guides photon path (i.e., guides photon to take certain path). In radiation-based imaging, photons may originate from unknown locations inside a subject, unlike in X-ray or CT where photons are emitted from a known source (or sources) position. Without collimators, photons from all directions may be recorded by a photon detector, and image reconstruction may become difficult. Therefore, collimators are employed to guide possible photon paths so that images can be reconstructed, similar to the role of lens in a photography camera. Although existing radiation-based imaging systems have been generally adequate for their intended purposes, they have not been entirely satisfactory in all respects. For example, existing collimators and detectors often have to be deployed with a tradeoff between imaging resolution and signal sensitivity, but not excel in both. Therefore, improvements on radiation-based imaging systems are desired.

SUMMARY

According to various embodiments, the present disclosure provides a radiation-based imaging system. The radiation-based imaging system includes a collimator configured to filter radiation emitted from a target object, the collimator including a plurality of apertures non-uniformly distributed on the collimator, wherein a largest acceptance angle of the plurality of apertures is not larger than 15°; and a detector for detecting the radiation that has passed through the collimator, wherein the collimator is spaced from the detector, such that a point on a top surface of the detector that faces the collimator is simultaneously illuminated by two or more of the plurality of apertures. In some embodiments, a point on the top surface of the detector is simultaneously illuminated by a percentage of the plurality of apertures, wherein the percentage is less than about 25%. In some embodiments, an amount of the plurality of apertures exceeds one thousand. In some embodiments, the plurality of apertures varies at least in one of aperture size, aperture shape, acceptance angle, length, and aperture pitch. In some embodiments, a distance between the collimator and the detector is from about 0.5 to about 10 times (such as from 1.5 to 10 times) of a thickness of the collimator. In some embodiments, the plurality of apertures forms a pattern that includes a repetitive basic pattern. In some embodiments, the repetitive basic pattern is a coded aperture pattern. In some embodiments, an illuminating area of one of the apertures substantially equals to an area of the repetitive basic pattern. In some embodiments, the collimator includes a first portion and a second portion, wherein the first portion includes through-holes uniformly distributed on the first portion and the second portion includes through-holes non-uniformly distributed on the second portion and corresponding to the plurality of apertures, such that a portion of the through-holes of the first portion is blocked by the second portion. In some embodiments, a thickness of the first portion is from about 2 to about 10 times of a thickness of the second portion. In some embodiments, the collimator is a first collimator and the detector is a first detector, the system further includes a second collimator and a second detector coupled to the second collimator, wherein the second collimator is attached to the second detector.

According to various embodiments, the present disclosure provides a radiation-based imaging system. The radiation-based imaging system includes a first collimator configured to filter radiation emitted from a target object, the first collimator including a first plurality of apertures that forms a first aperture pattern; a first detector associated with the first collimator for detecting the radiation that has passed through the first collimator; a second collimator configured to filter the radiation emitted from the target object, the second collimator including a second plurality of apertures that forms a second aperture pattern; and a second detector associated with the second collimator for detecting the radiation that has passed through the second collimator, wherein the target object is positioned between the first collimator and the second collimator, and wherein the first aperture pattern is different from the second aperture pattern. In some embodiments, the first collimator is in contact with the first detector, and wherein the second collimator is spaced from the second detector. In some embodiments, a distance between the second collimator and the second detector is from about 0.5 to about 7 times (such as from 1.5 to 7 times) of a thickness of the second collimator. In some embodiments, the first plurality of apertures is uniformly distributed on the first collimator, and wherein the second plurality of apertures is non-uniformly distributed on the second collimator. In some embodiments, the second aperture pattern includes a repetitive coded pattern. In some embodiments, the repetitive coded pattern is one of a uniformly redundant array (URA) pattern, a modified uniformly redundant array (MURA) pattern, and a perfect binary array (PBA) pattern. In some embodiments, directions the first and second detectors pointing toward have an offset angle.

According to various embodiments, the present disclosure provides a collimator for filtering radiation emitted by an object. The collimator includes a first portion including a first plurality of through-holes that are uniformly distributed; and a second portion including a second plurality of through-holes that are non-uniformly distributed, wherein the first and second portions are spaced apart and aligned in a way that photons emitted by the object traveling through some of the first plurality of through holes are blocked by the second portion. In some embodiments, the second plurality of through-holes forms a coded pattern. In some embodiments, the second portion is operable to slide with respect to a surface of the first portion facing the second portion, such that the aligned through-holes of the first and second pluralities of through-holes can be changed.

According to various embodiments, the present disclosure provides a method of misalignment correction in an imaging system. The method includes providing a collimator and a detector, the detector having a digitized pixel grid; illuminating the collimator with a flood light source; recording signal intensities in each pixel of the digitized pixel grid, wherein the signal intensities are caused by the illuminating of the collimator; deriving a descriptor from the recorded signal intensities; generating a series of offsets introduced to the digitized pixel grid; finding a selected offset from the series of offsets that optimizes the descriptor; and regenerating the digitized pixel grid based on an actual optimum offset derived from the selected offset. In some embodiments, the selected offset includes a pair of offset values in two orthogonal directions, respectively. In some embodiments, the descriptor is one of a contrast value, a peak value, and a valley value of the recorded signal intensities. In some embodiments, the contrast value is determined by a ratio of values at peaks and valleys of a signal intensity line corresponding to the signal intensities recorded at the digitized pixel grid. In some embodiments, the finding of the selected offset includes sweeping the series of offsets and picking the selected offset that maximizes or minimizes the descriptor. In some embodiments, the regenerating the digitized pixel grid includes adjusting the selected offset by a fixed offset to generate the actual optimum offset and regenerating the digitized pixel grid with the actual optimum offset.

BRIEF DESCRIPTION OF THE DRAWINGS

The present disclosure is best understood from the following detailed description when read with the accompanying figures. It is emphasized that, in accordance with the standard practice in the industry, various features are not drawn to scale and are used for illustration purposes only. In fact, the dimensions of the various features may be arbitrarily increased or reduced for clarity of discussion.

FIGS. 5A and 5B illustrate top views of part of a collimator with non-uniformly distributed apertures according to various aspects of the present disclosure.

FIG. 7 illustrates a step of decomposing an original image into a series of sub-images in a fast image reconstruction algorithm according to various aspects of the present disclosure.

FIGS. 8A, 8B, 8C, 9A, 9B, 9C, 10A, and 10B illustrate cross-sectional views of some embodiments of light-weight collimators according to some embodiments of the present disclosure.

FIGS. 11A, 11B, 12A, 12B, and 13 illustrate top views and cross-sectional views of some embodiments of radiation-based imaging systems with alignment adjustment.

DETAILED DESCRIPTION

Figure 1A:
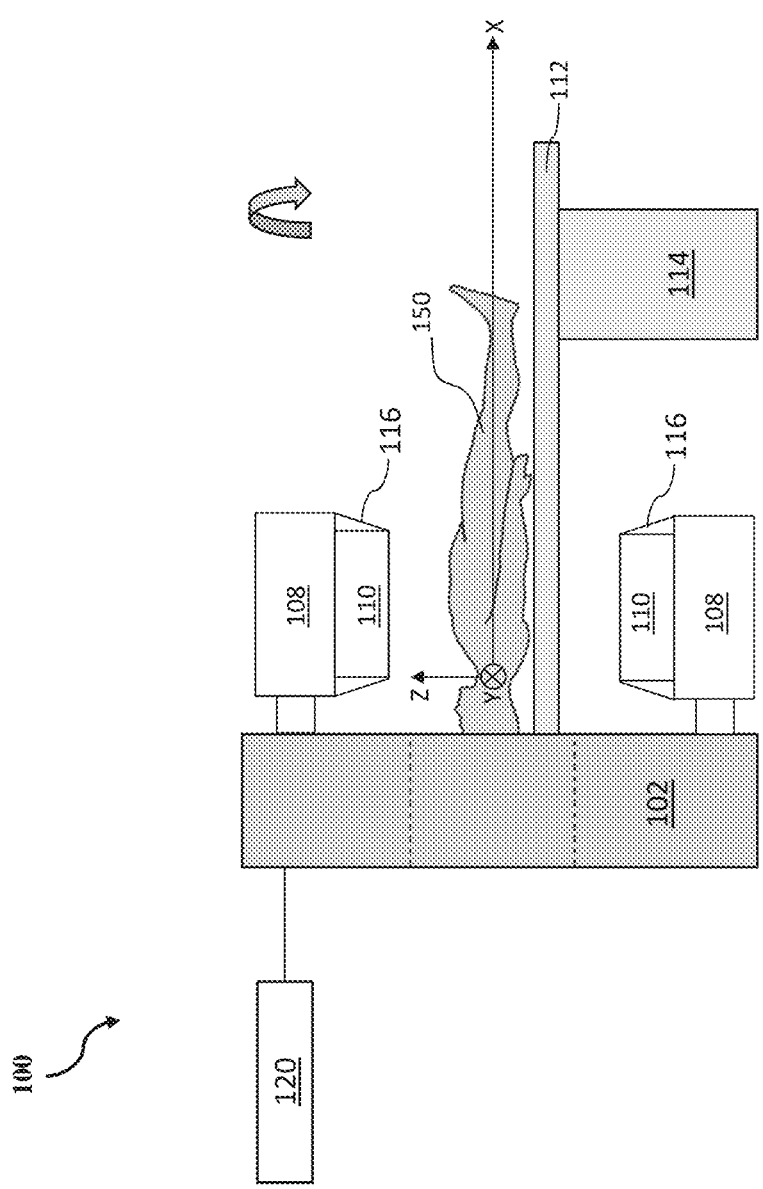
FIGS. 1A, 1B, and 1C are schematic diagrams of an exemplary radiation-based imaging system according to various aspects of the present disclosure.

The following disclosure provides many different embodiments, or examples, for implementing different features of the disclosure. Specific examples of components and arrangements are described below to simplify the present disclosure. These are, of course, merely examples and are not intended to be limiting. Any alterations and further modifications to the described devices, systems, methods, and any further application of the principles of the present disclosure are fully contemplated as would normally occur to one having ordinary skill in the art to which the disclosure relates. For example, the features, components, and/or steps described with respect to one embodiment may be combined with the features, components, and/or steps described with respect to other embodiments of the present disclosure to form yet another embodiment of a device, system, or method according to the present disclosure even though such a combination is not explicitly shown. In addition, the present disclosure may repeat reference numerals and/or letters in the various examples. This repetition is for simplicity and clarity and does not in itself dictate a relationship between the various embodiments and/or configurations discussed.

Moreover, a feature on, connected to, and/or coupled to another feature in the present disclosure that follows may include embodiments in which the features are in direct contact, and may also include embodiments in which additional features may interpose the features, such that the features may not be in direct contact. In addition, spatially relative terms, for example, "lower," "upper," "horizontal," "vertical," "above," "over," "below," "beneath," "up," "down," "top," "bottom," etc., as well as derivatives thereof (e.g., "horizontally," "downwardly," "upwardly," etc.) are used for ease of the present disclosure of one features relationship to another feature. The spatially relative terms are intended to cover different orientations of the device including the features. Still further, when a number or a range of numbers is described with "about," "approximate," and the like, the term is intended to encompass numbers that are within a reasonable range including the number described, such as within +/−10% of the number described or other values as understood by person skilled in the art. For example, the term "about 5 cm" encompasses the dimension range from 4.5 cm to 5.5 cm.

The present disclosure is generally related to collimators for use in radiation-based imaging, and more particularly to collimators with non-uniformly distributed apertures for use in nuclear medicine (molecular) imaging systems. The term "non-uniformly distributed apertures" refers to apertures (through-holes) of a collimator that vary in at least one of aperture profiles including but not limited to aperture size, aperture shape (including cross-sectional and longitudinal shape), aperture length, aperture pitch, and aperture orientation.

In radiation-based imaging, such as nuclear medicine (molecular) imaging systems, collimator and detector work in tandem to generate images that represent radiopharmaceutical distributions within a subject. Many nuclear medicine imaging systems, for example, single photon emission computed tomography (SPECT), and positron emission tomography (PET) imaging systems, use one or more detectors, to acquire imaging data, such as gamma ray or photon imaging data. Prior to acquiring images, a radiopharmaceutical is usually taken orally or injected into an object such as a patient. The radiopharmaceutical undergoes nuclear decay, emitting, either directly or indirectly through annihilation, gamma photons at certain rates and with characteristic energies. One or more detector units are placed around the object to record or monitor emissions. In many cases, for convenience of manufacturing and data processing, the detectors are organized in planar shape, therefore acquiring data in 2D matrix format, which are often referred to as projections. Based on the recorded information including position, energy and counts of such detected events, an image of the radiopharmaceutical distribution can be reconstructed to study the function of certain parts of the object (e.g., body parts of a patient).

However, existing collimator and detector designs suffer from various issues. For example, parallel-hole collimators are conventionally tightly coupled (or attached) to detectors in order to reduce cross-talk between sensing pixels in detectors, such that there is only one possible photon path to any sensing pixel. Generally, longer apertures of a collimator would benefit imaging resolution of the imaging system but deteriorate its signal sensitivity. Therefore, a length of apertures of a collimator has to be determined with a tradeoff between imaging resolution and signal sensitivity.

The present disclosure provides embodiments of collimator designs where a collimator with non-uniformly distributed apertures is deployed in a distance away from a detector, such that some areas of the detector are simultaneously illuminated by photons passing through more than one aperture. Stated differently, at least some apertures of the collimator have their respective illuminating areas on the detector overlapped with each other. By spacing a collimator from a detector and utilizing larger aperture size (or wider acceptance angle), effective length of apertures of the collimator is increased resulting in improved imaging resolution without sacrificing signal sensitivity. Also, in some embodiments of the present disclosure, apertures of a collimator have a repetitive pattern. In furtherance of the embodiments, the pattern may be one of a uniformly redundant array (URA) pattern, a modified uniformly redundant array (MURA) pattern, a perfect binary array (PBA) pattern, a random pattern, a pseudo random pattern, and other suitable patterns. The repetitive pattern allows a radiation-based imaging system to adopt a simplified image reconstruction algorithm to reduce computation complexity and to increase system performance. In various embodiments, a collimator may also adopt a light-weight design by having a thin plate defining apertures without fully filling closed holes. Accordingly, the new collimator designs improve performance of radiation-based imaging systems from various aspects.

Figure 1C:
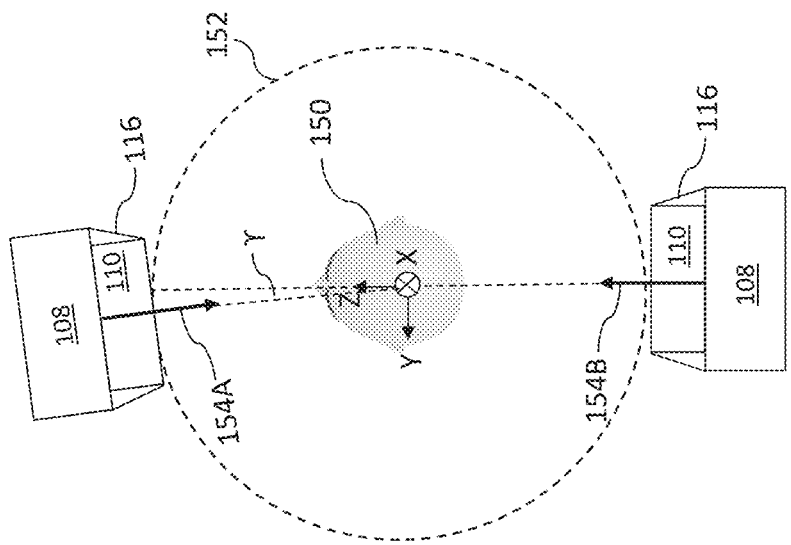
Figure 1B:
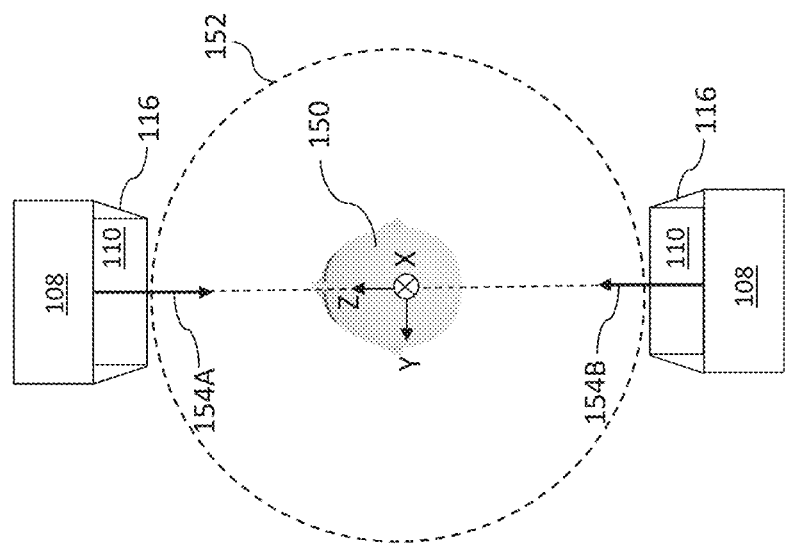

FIGS. 1A-1C illustrate an example radiation-based imaging system 100 (a nuclear medicine imaging system in particular) that incorporates features of the present disclosure according to some embodiments. FIG. 1A is a cross-sectional sideview of a portion of the system 100 in the X-Z plane. FIGS. 1B and 1C are axial views of the system 100 in the Y-Z plane in two embodiments. The imaging system 100 may be used to medically examine or treat a target object such as a patient. The imaging system 100 includes integrated gantry 102 that further includes rotating mechanism (e.g., a rotor oriented about a gantry central bore) that is configured to support and rotate one or more detectors 108 (two detectors 108 in opposing positions are shown) about an axial axis (e.g., X-direction as shown). In one embodiment as illustrated in FIG. 1B, two detectors 108 are operable to rotate along a circle 152 in opposing positions with normal directions 154A and 154B to the respective top surfaces of the two detectors 108 both pointing to the center of the circle 152 and in opposite directions. In an alternative embodiment as illustrated in FIG. 1C, two detectors 108 are similarly operable to rotate along the circle 152 in opposing positions with the normal directions 154A and 154B to the respective top surfaces of the two detectors 108 pointing to the center of the circle 152 as well. The difference is that the normal directions 154A and 154B in FIG. 1B are not exactly opposite but form a small angel T. The angel T may range from about 0.5° to about 200 depending on system performance needs, in accordance with some embodiments. The details regarding the setups in FIGS. 1B and 1C will be discussed later on. Each detector 108 works in tandem with a collimator 110. The collimator 110 is a device that guides photon path. In molecular imaging, photons may originate from unknown locations inside a subject, unlike in X-ray or CT where photons are emitted from a known source (or sources) position. Without collimators 110, photons from all directions may be recorded by detectors 108, and image reconstruction may become difficult. Therefore, collimators 110 are deployed to guide photon paths so that images can be reconstructed. The imaging system 100 further includes a patient table 112 coupled to a table support system 114, which may be coupled directly to a floor or may be coupled to the gantry 102 through a base. The patient table 112 is configured to be able to slide with respect to the table support system 114, which facilitates ingress and egress of a patient 150 into an examination position that is substantially aligned with the axial axis. A control console 120 provides operation and control of the imaging system 100, such as in any manner known in the art. For example, the control console 120 may be used by an operator or technician to control mechanical movements, such as rotating the rotor 104, moving, rotating, or tilting the detectors 108 and collimators 110, and sliding the patient table 112. The imaging system 100 further includes computer components (not shown), such as data storage units, image processors, image storage units, and displays, for acquiring data and reconstructing nuclear medicine images. In some embodiments, one or more computer components can be partially or entirely located at a remote location (e.g., using the cloud computing). In some embodiments, one or more of these components may exist locally or remotely.

In some embodiments, the detector 108 is a semiconductor detector, such as one based on cadmium telluride (CdTe), cadmium zinc telluride (CZT), or high purity germanium (HPGe). In some embodiments, the detector 108 is a scintillator (such as sodium iodide (NaI) or caesium iodide (CsI) based) detector. In some other embodiments, the detector 108 may also be a scintillator coupled with compact photo multiplier tubes (PMTs), silicon photomultiplier tubes (SiPMT), or avalanche photodiodes. One or more radiopharmaceuticals orally taken or injected into patient 150 undergo nuclear decay and may emit, either directly or indirectly through annihilation, radiation (e.g., gamma photons) at certain rates and with characteristic energies. The detector 108 is placed near patient 150 to record or monitor emissions. Based on recorded information such as position, energy, and counts of such detected events, an image of radiopharmaceutical distribution may be reconstructed to study the status or function of certain body parts on patient 150.

The collimator 110 includes plural walls (known also as septa) that define one or more apertures (also referred to as openings or through-holes). In various embodiments, septa are made of heavy metal such as lead or tungsten. The thickness of the septa, depending on the energy of photons, is large enough to stop the majority of the radiation so that the photons primarily pass through the small apertures on the plate. The thickness needs to be greater to image higher energy gamma rays. The collimator 110 is placed between detector 108 and an imaging object, such as the patient 150. The apertures of a collimator determine the directions and angular span (acceptance angle) from which radiation can pass through to reach certain position on the detector. Depending on number and geometrical placement of apertures, the collimator 110 may be a single-hole collimator, a multi-hole collimator, or a coded aperture collimator, or other suitable type of collimator.

The imaging system 100 may include other necessary parts for an imaging gantry such as connectors that couple parts together (e.g., connecting detector 108 and collimator 110 together), motors that cause parts to move, photon shielding components, a housing component that contains other parts, etc. For example, a coupling and shielding component 116 may connect detector 108 and collimator 110 such that both move (e.g., rotate) together, and prevent radiation (photons) from reaching detector 108 through paths other than collimator 110. In other embodiments, detector 108 and collimator 110 may move individually with respect to each other.

Figure 2B:
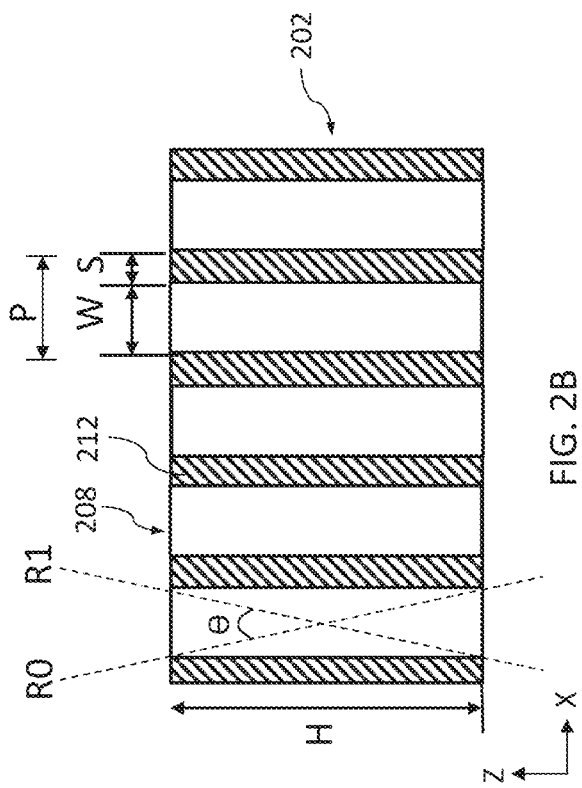
FIGS. 2A, 2B, 2C, 2D, 2E, and 2F provide perspective, cross-sectional, and top views of part of a collimator according to some embodiments of the present disclosure.
Figure 2A:
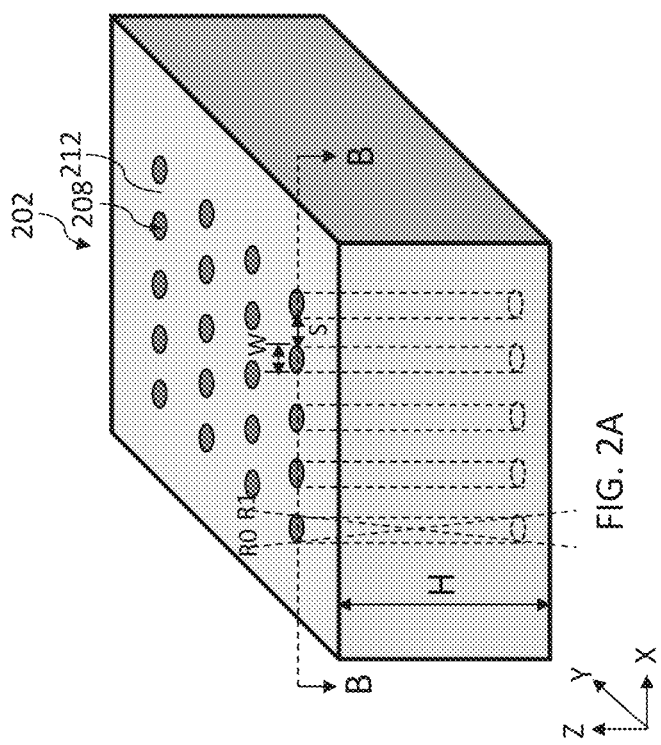

FIG. 2A shows a perspective view of an example multi-hole (or multi-aperture) collimator 202 and FIG. 2B shows a cross-sectional view (along B-B cut in FIG. 2A) of the collimator 202. The collimator 202 has numerous holes 208, each having a height H and a diameter (or width) W. The height H is also the thickness of the collimator 202. The holes 208 are also referred to as apertures, openings, or through-holes. The acceptance angle $\Theta$ of an aperture 208 is defined by the angle between two rays R0 and R1 traveling from an edge point on the upper opening of the aperture 208 to an opposing edge point on the lower opening of the aperture 208. Only incident photons (or radiation) traveling within the acceptance angle $\Theta$ can pass through the aperture 208 (without considering a small portion of rays that may penetrate the septa 212). As discussed above, the septa 212 are made of radiation absorbing heavy metal(s) or alloy, such as lead or tungsten. The septa 212 absorbs most radiation that do not emanate from (or travel at) the direction of interest. A collimator for higher energy radiation has much thicker septa than a collimator for lower energy radiation. The septa are generally designed so that septal penetration by unwanted photon does not exceed 5% and in some instances does not exceed 1%. It should be noted that radiation or photon blocked or absorbed by a collimator does not require a 100% blocking rate because a small percentage of photons (e.g., 5% or less) may still penetrate through the thickness of the radiation absorbing material. In other words, blocking (or other similar terms) means that vast majority of the photons (e.g., 95% or more, or 99% or more) are absorbed by the radiation absorbing material.

The collimator 202 provides positional information for detected photons by restricting the incident photon acceptance angle $\Theta$. Generally, the smaller the acceptance angle $\Theta$, the higher the imaging resolution provided by the collimator 202. The collimator 202 may have a large number of substantially identical, long and narrow apertures 208 placed side by side and in parallel to each other. The long and narrow apertures come with small acceptance angle $\Theta$ and accordingly high imaging resolution. The collimator 202 may have a thickness H larger than 15 mm, such as 20 mm to 70 mm, with an aperture diameter (or width) W around 1 mm to 5 mm, thereby providing a large aspect ratio (H/W) and small acceptance angle $\Theta$. The acceptance angle $\Theta$ of the parallel-hole collimator 202 is limited to a small angle, such as not greater than 15°. If the acceptance angle $\Theta$ is too large (such as greater than 15°), the imaging resolution provided by the particular parallel-hole collimator is considered undesirably low. Unless otherwise specified, the acceptance angle $\Theta$ of the example collimators in the present disclosure is not greater than 15°. In addition to the holes in FIG. 2B that are rectangular in the "x-z" cross-section, the concept of acceptance angle can be extended to holes in other forms, such as holes in converging or diverging collimator, where the holes can be of trapezoidal shape and may be slanted, representing the largest angle difference of rays that may pass through the hole.

The collimator 202 illustrated in FIG. 2A is a parallel-hole collimator with uniformly distributed apertures. In the illustrated embodiment, the apertures 208 are substantially identical, each having the same height H and the same diameter or width W, except for variations caused by fabrication precision limitations. Accordingly, each aperture has the same acceptance angle $\Theta$ that is small (such as not larger than 15°, such as about 5° in a particular example). The aperture pitch P is also substantially the same on the collimator 202. In other words, the aperture spacing S (septa thickness) is uniform on the collimator 202. Herein, apertures with uniform aperture shape, aperture size, aperture length, and aperture pitch are termed as "uniformly distributed apertures."

Figure 2D:
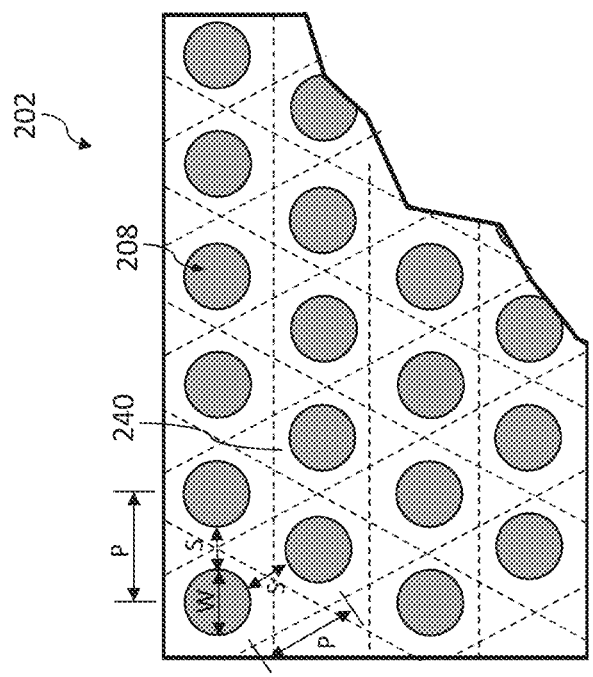
Figure 2C:
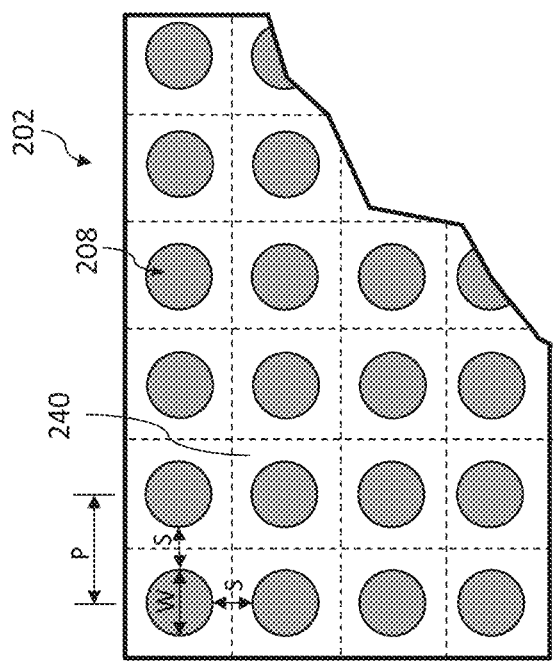
Figure 2F:
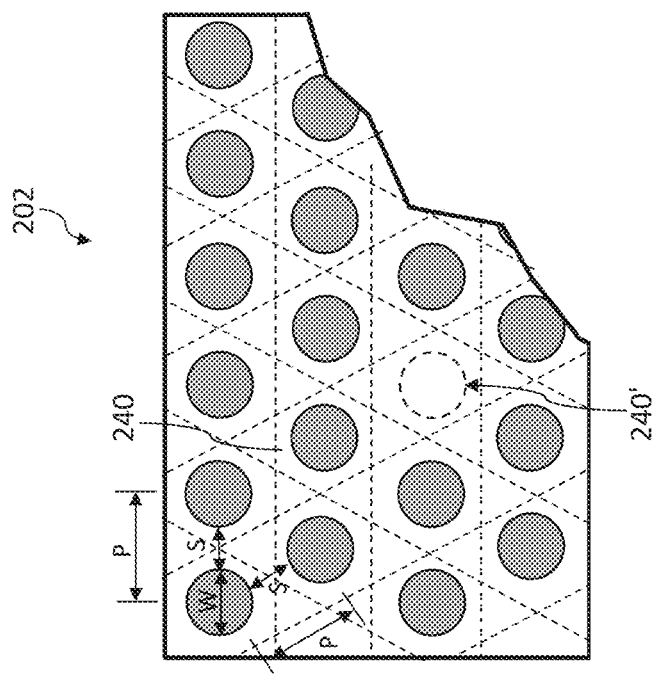
Figure 2E:
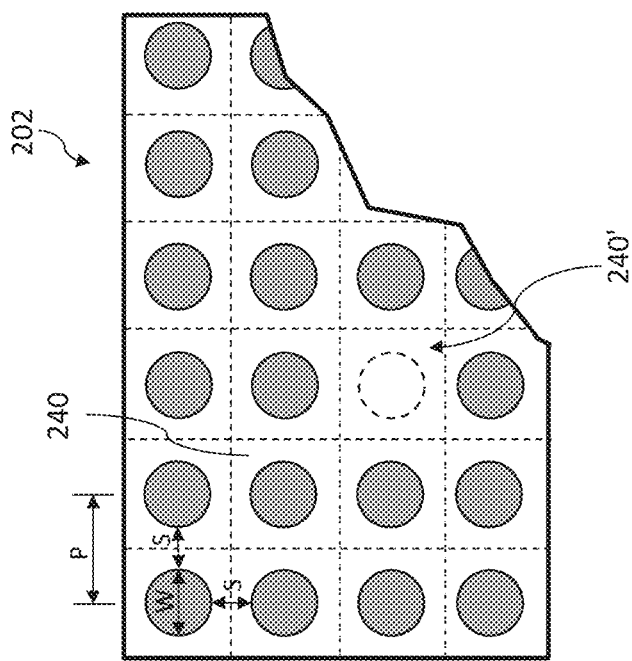

FIGS. 2C and 2D illustrate top views of two arrangements of parallel-hole collimators (such as the collimator 202) with uniformly distributed apertures, while other arrangements are possible and do not depart from the spirit and scope of the present disclosure. In FIG. 2C, apertures 208 are arranged in orthogonal rows and columns to form an orthogonal two-dimensional grid arrangement. Each aperture 208 can be regarded as being aligned with a unit grid 240 of a square shape in a grid network (represented by dashed lines in FIG. 2C). Two adjacent apertures 208 have the same pitch P, where P=W+S, W is the width (or diameter) of the aperture 208 and S is the minimum spacing (or septa thickness) between two adjacent apertures 208. In FIG. 2D, apertures 208 are arranged in a staggered fashion with a succession of rows adjacent to each other and two adjacent rows being offset from each other by a distance (or an offset). The offset may be W in an embodiment or other suitable values in alternative embodiments. Each aperture 208 can be regarded as being aligned with a unit grid 240 of a hexagonal shape in a grid network (represented by dashed lines in FIG. 2D). Two adjacent apertures have the same pitch P, where P=W+S, W is the width (or diameter) of the aperture 208 and S is the minimum spacing (or septa thickness) between two adjacent apertures 208. In some alternative embodiments (not shown), apertures 208 may be aligned with a unit grid 240 of a honeycomb shape of a grid network. FIGS. 2E and 2F illustrate variations of FIGS. 2C and 2D, respectively. One or more of the unit grids 240 may be designed to have no aperture(s) there-through, which is equivalent to having an aperture (represented by a dashed circle in FIGS. 2E and 2F) that is filled up (or closed) by the septa material. Such aperture arrangement is considered as having a varying aperture pitch or having closed holes, and thus not in the category of parallel-hole collimators with uniformly distributed apertures. In other words, the apertures in FIGS. 2E and 2F are non-uniformly distributed.

Figure 3:
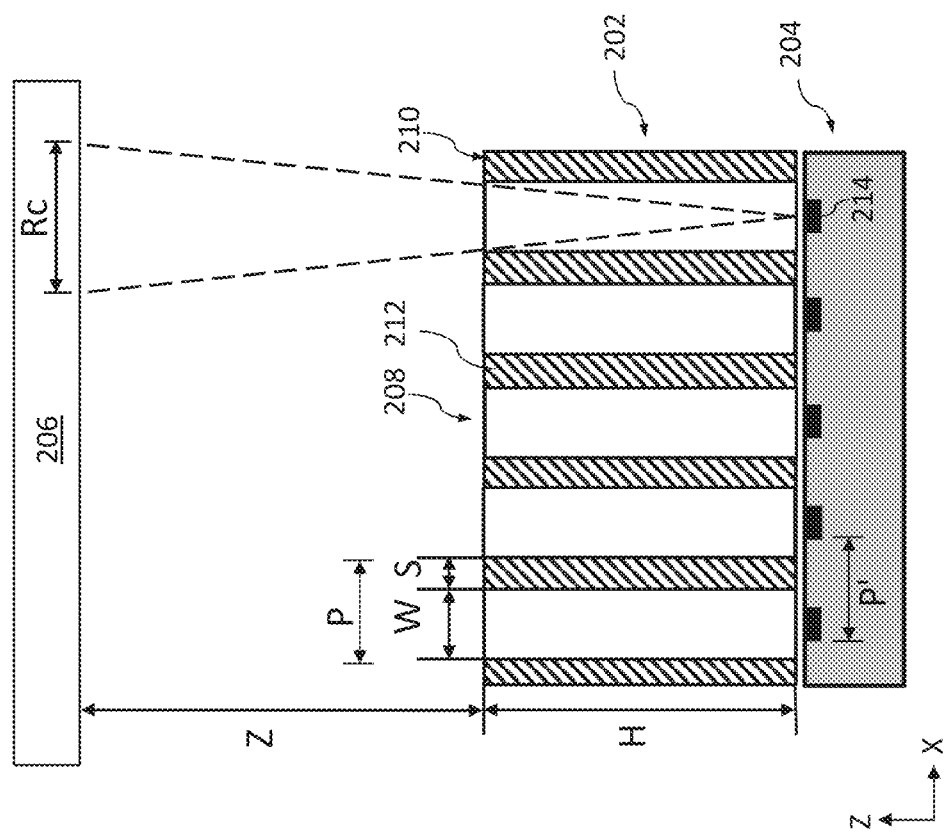
FIG. 3 is a cross-sectional view of part of a radiation-based imaging system according to some embodiments of the present disclosure.

FIG. 3 is a schematic cross-sectional view of a collimator 202 as illustrated in FIG. 2B and a detector 204 that work in tandem to generate images that represent radiopharmaceutical distributions within a target object 206 (e.g., a patient). The collimator 202 is positioned between the target object 206 and the detector 204 and configured to filter radiation by blocking certain photons and passing through other photons. In the illustrated embodiment, coupling and shielding components connecting the collimator 202 and the detector 204 are omitted for the sake of simplicity. In the present embodiment, the collimator 202 is a parallel-hole collimator where the apertures or holes in the collimator 202 have a rectangular cross-section and are arranged parallel to each other. In alternative embodiments, the apertures or holes in the collimator 202 may have a diverging cross-section, a converging cross-section, or some other cross-sectional shape.

The detector 204 includes an array of sensing pixels 214, such as a rectangular array, a square array, or other suitable arrays of pixels 214. In operation, each sensing pixel 214 records or monitors individually the amount of radiation incident thereon and generates signals (e.g., voltage or current) in association with the amount of radiation. The sensing pixels 214 may be of substantially the same size and the same shape (e.g., circular, rectangular, or square shape). The size of the sensing pixels 214 may range from about 1×1 mm² to about 5×5 mm² in various embodiments. The sensing pixel pitch P' of the array may range from less than 1 mm to about 6 mm in various embodiments. In an example, a CZT or silicon multiplier (SiPM) based detector 204 can be fabricated in a size of 4 cm×4 cm, consisting of an array of 16×16 sensing pixels with a unit pixel size of 2.5 mm×2.5 mm. In some embodiments, the detector 204 includes appropriate electronic circuits (e.g., ASICs) to collect and process the signals generated from the sensing pixels 214. In some other embodiment, the sensing pixels 214 are not physically distinctive from each other and are mere results of digitization of a continuous detector surface, as in the case of most PMT-based detector systems. For example, the detector surface may be digitized as a grid network that is same as the grid network in the collimator 202 with each unit grid in the detector surface corresponding to an aperture in the collimator 202.

In FIG. 3, for simplicity, assume that the sensing pixel pitch P' substantially equals the aperture pitch P, such that each sensing pixel 214 is directly under a corresponding aperture 208. Further, the collimator 202 is tightly coupled (or attached) to the detector 204 with minimal spacing between the collimator 202 and the detector 204 such that photons are allowed to only travel along the apertures 208 to reach corresponding sensing pixel 214 immediately under it, although minimal or negligible cross-talk is possible (e.g., photons may pass through the septa or photons may pass through one aperture but hit a sensing pixel directly under another, different, aperture). In the present disclosure, the terms "tightly coupled to" and "attached to" both refer to a spacing between a collimator and a detector being less than half of a thickness of the collimator including the instance where the collimator 202 and the detector 204 are in physical contact.

For a parallel-hole collimator, its imaging resolution degrades quickly when the imaging source moves away from the collimator. For a collimator with an aperture size W and length (or effective length) of $H_e$, for a target object 206 located at a vertical distance Z above the collimator top surface 210, the imaging resolution of the collimator, $R_c$, is given by equation (1) below:

$$R_c = (H_e+Z)/H_e * W = (1+Z/H_e) * W. \qquad (1)$$

The effective aperture length $H_e$ is given by $H_e = H - 2/\mu$, where H is the aperture length and is a linear attenuation coefficient of the collimator material. For lead, at 150 keV, $=22.43$ cm$^{-1}$, and $2/\mu \approx 1$ mm. The aperture length H is usually greater than 20 mm, therefore $H \approx H_e$. For the sake of simplicity, H and $H_e$ are used interchangeably herein unless they have a meaningful difference. As a simple way to look at Eq. (1), the imaging resolution $R_c$ equals to an area at a distance Z that can be seen through an aperture from the bottom of the aperture, as shown in FIG. 3.

As seen from Eq. (1), the imaging resolution $R_c$ increases linearly with distance Z. And at the same distance Z, $R_c$ is smaller (i.e., having a better imaging resolution) if $H_e$ is bigger, meaning that the imaging resolution would be improved for longer apertures (i.e., larger H). However, longer apertures adversely affect signal sensitivity in an inverse-square relation. Let G denote the collimator efficiency, defined by the ratio of the amount of radiation rays (e.g., gamma rays) passing through the collimator to the amount of the radiation rays emitted by the source, then G is in direct proportion to $H_e^{-2}$ (i.e., $G \propto H_e^{-2}$). Hence aperture length H has to be chosen to balance imaging resolution and signal sensitivity.

Figure 4:
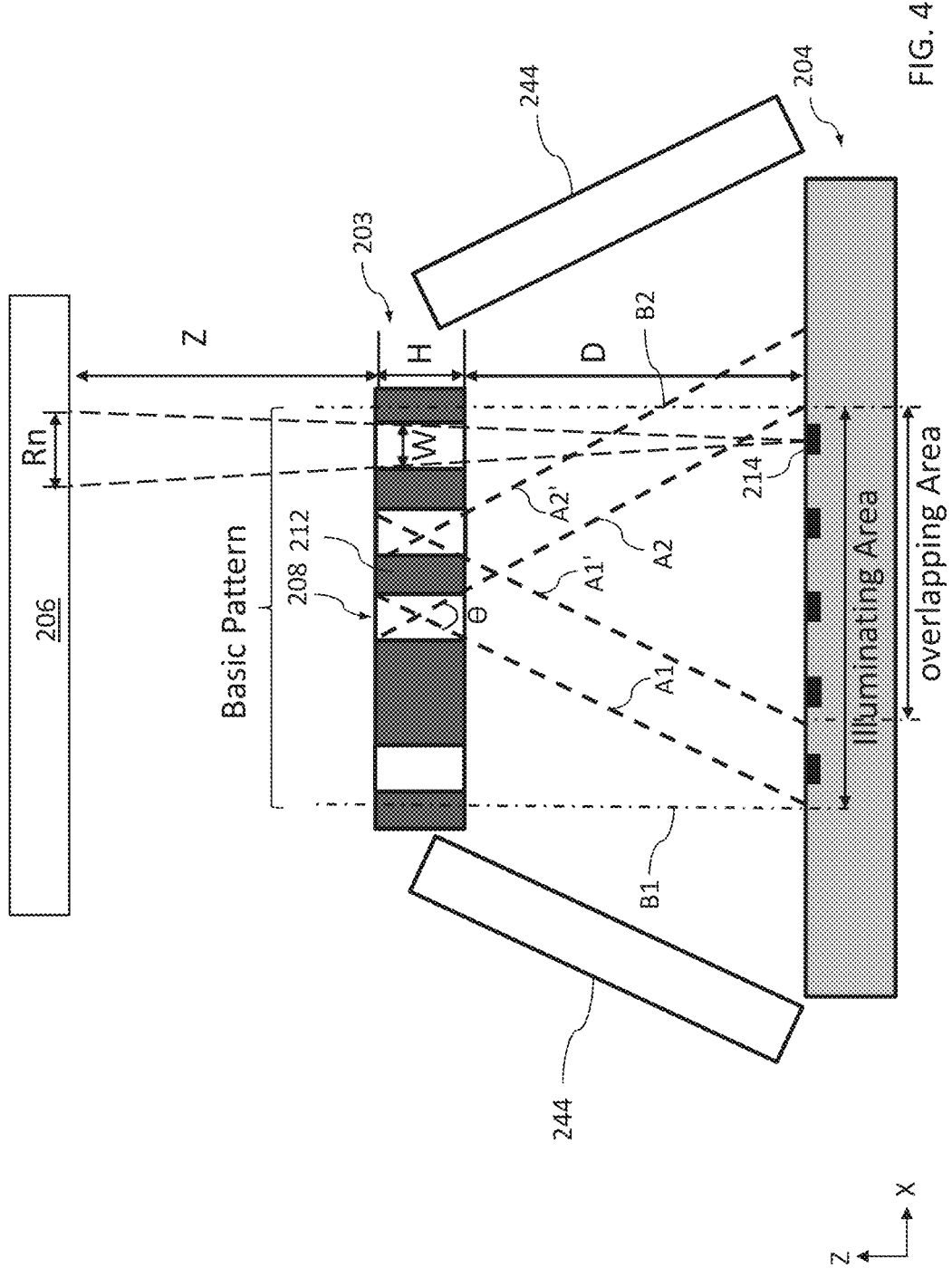
FIG. 4 is a cross-sectional view of part of a radiation-based imaging system according to some other embodiments of the present disclosure.

FIG. 4 illustrates an alternative collimator design termed as a "spread field imaging (SFI) collimator", which provides an increased equivalent aperture length, therefore higher imaging resolution, without sacrificing signal sensitivity. In comparison to the parallel-hole collimator 202 as shown in FIG. 3, the SFI collimator 203 as shown in FIG. 4 has at least two distinctive features. First, the spacing D between the SFI collimator 203 and the detector 204 is significantly increased compared with the configuration in FIG. 3. Second, the apertures 208 of the SFI collimator 203 are not all identical and differ in at least one aspect. These are further discussed below.

The spacing D between the SFI collimator 203 and the detector 204 is increased to allow photons passing through one aperture 208 to be incident on an area of the detector 204 that extends beyond the aperture 208. In other words, radiations from the target object 206 travel through an aperture 208 and spread and illuminate an area on the detector 204 that is substantially larger than the size of the aperture 208 and extends to areas that are directly underneath other neighboring apertures. In contrast, when the collimator 202 is tightly coupled to the detector 204 such as shown in FIG. 3, radiations from a target object 206 that travel through one aperture 208 only illuminate an area on the detector 204 that substantially equals the size of the aperture 208. As illustrated in FIG. 4, an incoming photon incident between lines A1 and A2 that define acceptance angle Θ would travel through the aperture 208 and arrive at the detector 204 and "illuminate" the detector 204. The surface area of the detector 204 bounded by lines defining acceptance angel Θ of an aperture 208 is denoted as the illuminating area of the respective aperture 208. For example, the illuminating area of the center aperture 208 is defined by a surface area of the detector 204 between the lines A1 and A2 that intersect the detector 204. An illuminating area's size and shape depend on the corresponding aperture's profile and the spacing D between the collimator 202 and the detector 204. In some embodiments, an illuminating area of an aperture 208 on the detector 204 is at least twice the size of the corresponding unit grid which includes the corresponding aperture 208 and half of the septa surrounding the corresponding aperture 208 (note that the boundary of a unit grid lies in the middle of septa between the unit grid and neighboring unit grids). Further, an illuminating area of one aperture 208 may overlap with illuminating areas of its neighboring apertures. For example, more than 10%, more than 20%, or even 50% (considering only radiation that pass through the aperture 208 and excluding radiation that penetrate the septa surrounding the aperture 208) of an illuminating area may be overlapped with other illuminating areas in various embodiments. FIG. 4 illustrates an overlapping area between the illuminating area defined by lines A1 and A2 under the aperture 208 and another illuminating area defined by lines A1' and A2' under a neighboring aperture. In other words, a point (or a sensing pixel 214) in the overlapping area of the detector 204 may receive radiations from more than one aperture 208. Furthermore, in some embodiments, any sensing pixel 214 in the detector 204 is simultaneously illuminated by no more than a percentage of the number of the apertures 208, wherein the percentage is less than about 25%. In some embodiments, the percentage is less than 10%, less than 5%, or even less than 2%. In some other embodiments, the illuminating area of any aperture is no more than a percentage of the total illuminating area (by all holes) of the coupled detector 204, wherein the percentage is less than 10%, less than 5%, or even less than 2%. In comparison, holes in coded aperture or multi-pinhole collimators generally illuminate a larger percentage of total illuminating areas than the embodiments of the present disclosure. For example, the illuminating area of a hole in those collimators may be greater than 25% or even greater than 40% of the total illuminating area of all holes in the respective collimator, which introduces large amount of cross-talk to the imaging system. By limiting the illuminating area of any hole to be no more than 10%, 5%, or even 2% (depending on system performance needs) of the total illuminated area (by all holes) of the coupled detector, cross-talk from different apertures is effectively reduced and hence good performance on the imaging resolution and signal sensitivity can be achieved.

Shielding 244 (usually with heavy metal materials) is provided along the peripheral region to cover (or seal) the space between the collimator 203 and the detector 204 to prevent radiation reaching the detector 204 through that space. Notably, although FIG. 4 shows gaps between the shielding 244 and the SFI collimator 203 and between the shielding 244 and the detector 204, it is for illustration purpose only. In various embodiments, shielding 244 is deployed to provide a closed (or sealed) area such that only radiations through the collimator 203 can arrive at the detector 204.

In the present embodiment, the apertures 208 of the SFI collimator 203 are not all identical. They may differ in aperture shape, aperture size, or even aperture length. If aperture sizes are different, the acceptance angle Θ may vary, but the largest acceptance angle Θ remains not greater than 150 in the present embodiment. As discussed above, an acceptance angle Θ not greater than 150 provides a desirable imaging resolution. Also, for a given collimator thickness H, smaller acceptance angle Θ translates to smaller aperture size, and consequently smaller collimator dimensions. An acceptance angle Θ not greater than 150 provides a good compromise between a compact collimator design and manufacturing difficulties (e.g., mechanical tolerance). Further, an acceptance angle Θ greater than 150 increases cross-talk from adjacent apertures and results in deteriorated resolution and increased complexities in post imaging processing. In some applications, an acceptance angle Θ can be less than about 10°, or even less than about 5°, in order to achieve a higher imaging resolution and less cross-talk based on system performance needs. In some embodiments, some of the apertures 208 of the SFI collimator 203 may be closed, meaning substantially blocked and not allowing photons to pass through. Accordingly, aperture pitch may also vary across the collimator 203. For example, in FIG. 5B, the pitch and septum around 208' is relatively different than other septa. Such apertures with non-uniformity in at least one parameter of aperture profiles (e.g., aperture shape, aperture size, aperture length, and aperture pitch) are referred to as "non-uniformly distributed apertures." FIG. 5A illustrates an embodiment of an SFI collimator 203 with different aperture shapes (e.g., circle and square), different aperture sizes, and different aperture pitches (due to blocked apertures represented by dashed circles). In FIG. 5A, each aperture 208 aligns with the respective unit grid 240 (e.g., center-to-center alignment). FIG. 5B illustrates yet another embodiment of an SFI collimator 203, in which there is at least one aperture 208' offset from its respective unit grid 240. The SFI collimator 203 with such aperture arrangement is also regarded as a parallel-hole collimator with non-uniformly distributed apertures. It is noted that FIGS. 5A and 5B merely show a portion of an SFI collimator 203. In an embodiment, the total number of apertures 208 on the collimator 203 exceeds one thousand (1,000), such as about two thousand (2000), five thousand (5000), ten thousand (10,000), thirty thousand (30,000), and even one hundred thousand (100,000). The large number of apertures are beneficial for higher sensitivity, good coverage of field of view (FOV), and better use of detector area because each aperture only illuminates a small percentage of the surface area of the detector 204 and there is significant cross-talk or multiplexing between apertures 208.

Figure 6A:
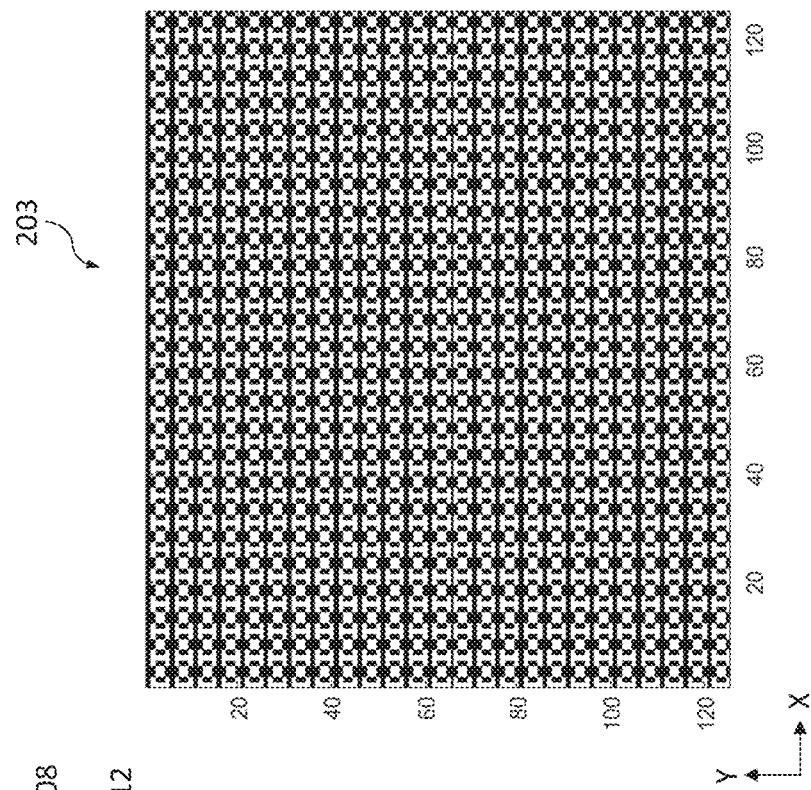
FIGS. 6A, 6B, and 6C illustrate top views of a collimator with a repetitive basic pattern according to some embodiments of the present disclosure.
Figure 6B:
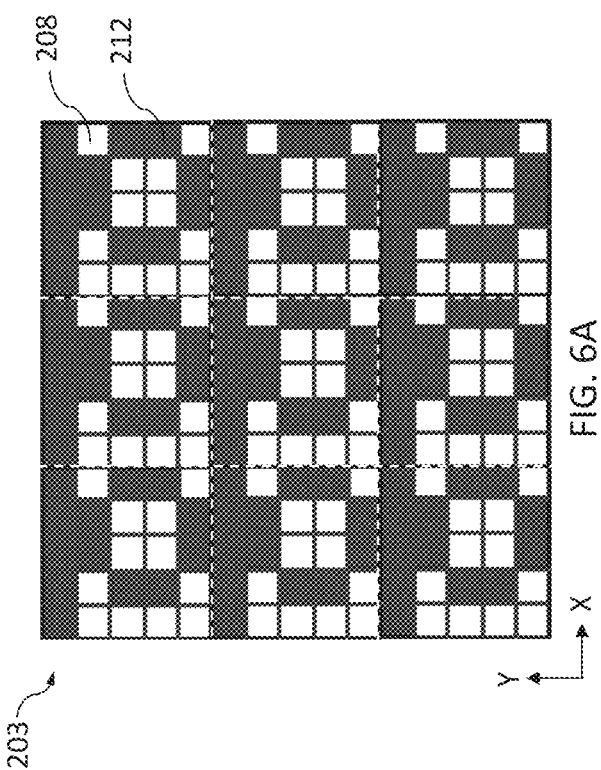
Figure 6C:
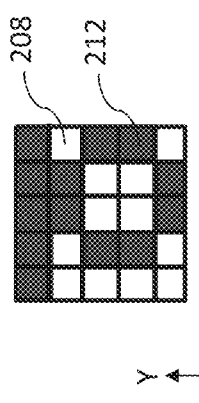

In some embodiments, a portion or all of the apertures 208 in the collimator 203 can be arranged in repetitive patterns, such as a repetition of patterns of size 3×3, 4×4, 3×5, 5×5, etc. The repetitive pattern is referred to as a basic pattern. In some embodiments, the basic pattern has odd number of rows and/or columns such that there is one central hole in the basic pattern, which can be advantageous in processing data. FIG. 6A illustrates a top view (or a portion of a top view) of an embodiment of the SFI collimator 203. At least a portion of the SFI collimator 203 includes a repetition of a basic pattern of 5×5 unit grids, with one basic pattern illustrated in FIG. 6B where white pixels represent open apertures and grey pixels represent closed apertures. The open apertures are surrounded by septa. The dotted lines in FIG. 6A represent the boundaries among the basic patterns. In the illustrated embodiment, an aperture aligns with a unit grid of square shape and may expand to the size of the whole unit grid. The basic pattern can be a coded aperture pattern, such as a URA, a MURA, a PBA, a random or pseudo random pattern. In some embodiments, the number of repetitive patterns is more than 2×2, such as 3×3, 3×5, 5×5, etc. In FIG. 6A, the illustrated basic pattern is a MURA 5 pattern and is repeated 3 times in X-direction and 3 times in Y-direction in forming a collimator (or a portion of a collimator) of a size 15×15. In various embodiments, a basic pattern can be repeated in X-direction and Y-direction any times, respectively, to fit a need of system requirement. FIG. 6C illustrates a top view of another embodiment of an SFI collimator 203 (or a portion thereof) where a basic pattern of MURA 5 is repeated 25 times in X-direction and 25 times in Y-direction in forming a collimator (or a portion of a collimator) of a size 125×125. In the illustrated embodiments, shape and size of the apertures are identical. In some embodiments, the apertures can be different in shape, in size, or both.

Referring back to FIG. 4, the spacing D between the collimator 203 and the detector 204 can be chosen such that the illuminating area of each aperture 208 on the detector 204 is the same as or no greater than a repetitive basic pattern but greater than at least twice of the aperture spacing (pitch). The size of an illuminating area of an aperture 208 on the detector 204 substantially equals to the size of a basic pattern of the collimator 203, such as illustrated by the dotted lines B1 and B2 in FIG. 4. As will be discussed in further details below, having the size of an illuminating area substantially equal to (or being an integer multiple of) a basic pattern provides a fast image reconstruction algorithm that significantly increases system efficiency and accuracy. As a result, the spacing D between the collimator 203 and the detector 204 is optimized when it is greater than half of the aperture length (collimator thickness) H. In various embodiments, D may be less than 10 times of H, for example between 1.5 and 10 times of H, between 1 and 7 times of H, between 1.5 and 7 times of H, or some other suitable range. If D is too small, such as less than 1.5 times H, the effect on resolution improvement is not significant. On the other hand, if D is larger than 10 times of H, cross-talk from neighboring apertures would be high and cause increased complexity and resolution degradation during image reconstruction. In some examples, D is about 1 time, 1.5 times, 2 times, 2.5 times, 3 times, or 3.5 times of H.

Still referring to FIG. 4, for a sensing pixel 214 of the detector 204, the area that can be seen through an aperture directly above it, also referred to as the imaging resolution $R_n$, is given by Eq. (2) below:

$$R_n=(H+D+Z)/(H+D)*W. \quad (2)$$

Note that the difference between Eq. (1) and Eq. (2) is that $H_e$ in Eq. (1) is replaced by (H+D) in Eq. (2), essentially extending the aperture length by D, therefore allows the imaging resolution to be significantly improved. $R_n$ can be smaller than $R_c$ even if aperture size, W, is increased for higher signal sensitivity.

The fact that photons may pass through one aperture and then hit a detector area directly underneath another aperture means there is cross-talk or multiplexing. In comparison, for any sensing pixel on the detector surface when a parallel-hole collimator (e.g., the collimator 202 as shown in FIG. 3) is equipped, there is only one aperture that photon can pass through and reach it (excluding septa penetration which is an effect to be suppressed in parallel-hole collimator design). This cross-talk effect usually degrades resolution because there are multiple possible paths for a photon detected at a detector location, and for a source at a certain point there are multiple apertures the radiation rays may pass through to reach the detector. And this is the case if all apertures are essentially identical as in a parallel-hole collimator.

On the other hand, regarding the SFI collimator 203 as shown in FIG. 4, the apertures are not all identical. More specifically, the apertures within the visible area of a sensing pixel on the detector surface are not all identical (the visible area here means the congregates of all apertures that a photon may pass through to reach that sensing pixel on the detector surface). As a result, sources close to each other will project different shadows on the detector because the aperture patterns below them are different. These differences help the reconstruction algorithm to recover the original source distribution, i.e., the object image, at a high resolution similar to $R_n$. The detector surfaces are usually digitized as a network of grids, and each grid represents a boundary of a sensing pixel. In some embodiments, the aperture patterns seen by neighboring sensing pixels are different.

Similar to SPECT imaging, images (also referred to as projections) can be acquired from multiple angles by rotating the set of coupled collimator (such as the collimator 203) and detector (such as the detector 204) around a target object. In this acquisition mode, the coupled collimator and detector are moving together with no relative motion between them. A forward projection p at a certain angle α can be written as $$\hat{p}_\alpha(i)=\Sigma_j f(j) K\alpha(i,j) \quad (3)$$

where i and j are indices of detector pixel and object image voxel, f(j) is the value of voxel object j, and Kα(i,j) is the probability of a photon emitted from voxel j being detected at pixel i when the camera is at angle α. To reconstruct the original object image f, a method to use is an MLEM algorithm where f can be found iteratively $$f_i^{(k+1)} = \frac{\hat{f}_j^{(k)}}{\Sigma_{i=1}^I K_{ij}} \sum_{i=1}^{I} \frac{p_i K_{ij}}{\Sigma_{j=1}^J K_{ij} \hat{f}_j^{(k)}} \quad (4)$$

or $$f^{(k+1)}(j) = \frac{f^{(k)}(j)}{\Sigma_{i,\alpha} K\alpha(i,j)} \sum_{i,\alpha} \frac{p(i,\alpha) K\alpha(i,j)}{\Sigma_j K\alpha(i,j) f^{(k)}(j)} \quad (5)$$

where $f^{(k)}(j)$ is the object image at $k^{th}$ iteration, and p(i,α) is the measured projection at detector pixel i and angle α. This algorithm has three steps—forward projection, calculating ratio, and back-projection. A variation of this algorithm is called OSEM, where the projections are divided into N subsets, and computation starts with several iterations using one subset of projections, and moves onto the next subset until all subsets have been computed. The process may repeat with different subset divisions and different number of iterations for each subset.

The algorithm as shown in Eq. (5) is extremely time consuming and requires enormous storage for the K matrix considering the large number of voxels and pixels, multiplied by the number of angles. The projection at one angle can be digitized as from 64×64 to up to 512×512 pixels, and usually acquisition from 60 or 120 angles is needed. And the object image often has 128×128×128 or 256×256×256 voxels. Therefore the matrix Kα(i,j) is extremely large.

Figure 7:
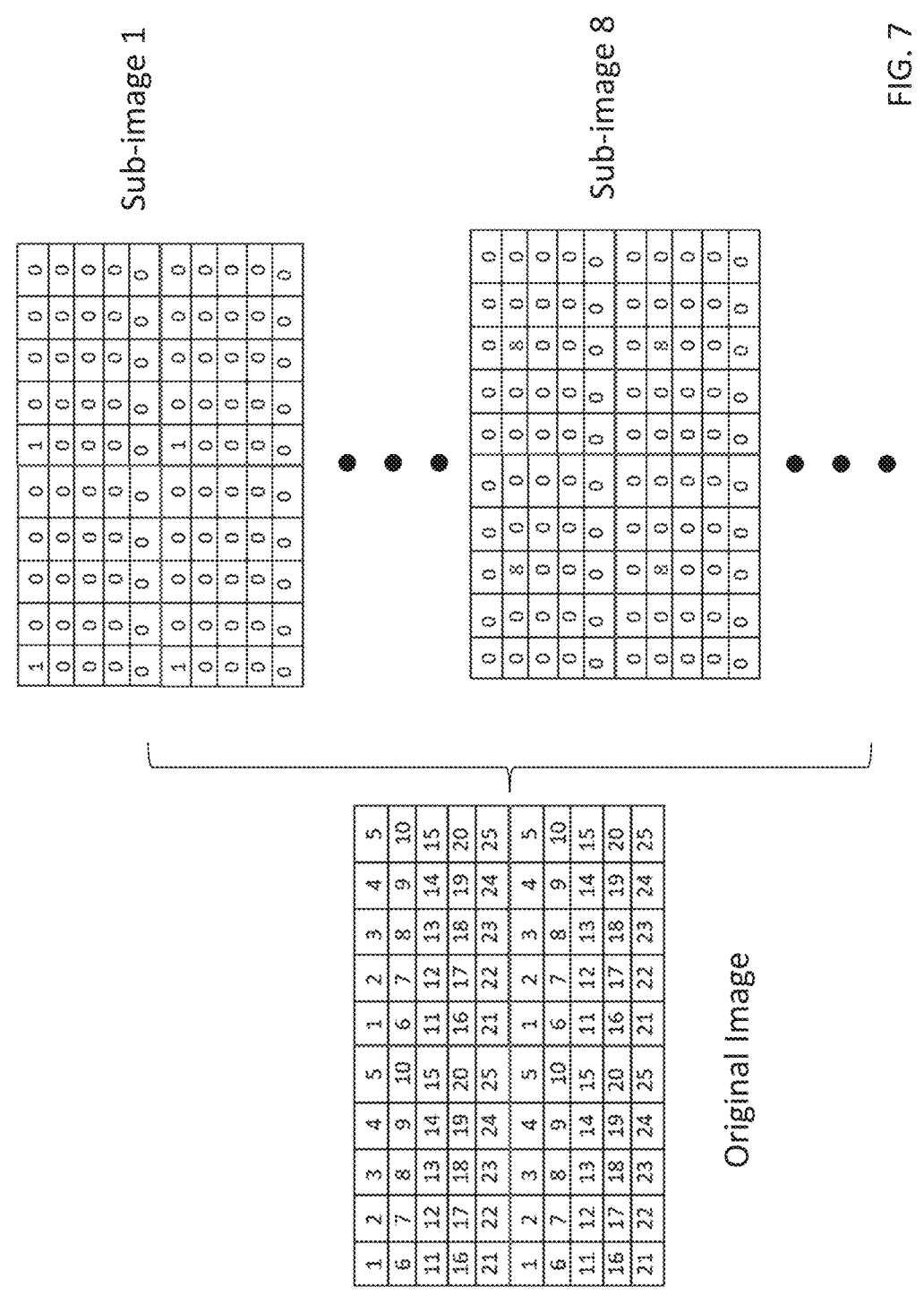

When the apertures are made up of repetitive basic patterns and the respective through holes in all repetitive patterns have the same shape and dimensions (even though the holes may differ in the basic pattern), the matrix K and the algorithm can be simplified. Generally, for a repetitive basic pattern of a size X×Y (X and Y can be different), there is only a number of patterns that equals a multiple of the product of X×Y that a point source may project on the detector. Shown in FIG. 6A or FIG. 6B is an example where the repetitive pattern is a 5×5 (X=Y=5) MURA 5 pattern. Let m be the index of holes (grid units, including open and closed holes) in the basic pattern, m=1, . . . 25. In this example, consider a plane located at distance Z from the collimator 203 (see FIG. 4), a point source at any point on that plane projects a pattern on the detector 204, where the size of projected pattern is much smaller than the size of detector, and there are only X×Y=25 patterns a point source may project on the detector, depending on the index of the aperture right below it (except in border region), denoted as $psf_{m,Z}(x,y)$ where $x=-M, \ldots M$ and $y=-N, \ldots, N$. Here the detector pixel size is the same as the collimator pitch (hole inter-spacing) or a fraction of that. Therefore, the 25 patterns can be indexed by the aperture in the basic 5×5 pattern. In the meantime, the object image at distance Z, denoted as $f_Z$, whose pixel (also called voxel) size is the same as the collimator pitch (hole inter-spacing) and the pixels are aligned with the collimator pitch, can be divided into 25 sub-images of the same size as $f_Z$, where in each sub-image the pixels on top of the aperture of the same index are kept the same, and the rest of the pixels are set to 0, as illustrated in FIG. 7. Let m be the pattern index, then a slice of object image at distance Z, $f_Z$, can be denoted by sub-images, $f_Z(j, m)$, given by $$f_Z(j,m) = \begin{cases} f_Z(j) & j \text{ is on top of a hole with index } m \\ 0 & \text{otherwise} \end{cases} \quad (6)$$

This way the forward projection step for object image at Z in Equation (5) can be rewritten as $$\hat{p}_\alpha(Z) = \Sigma_j K\alpha(i,j) f_{z,\alpha}^{(k)}(j) = \Sigma_m f_{z,\alpha}^{(k)}(j,m) * psf_{m,Z} \quad (7)$$

where $\hat{p}_\alpha(Z)$ is the forward projection calculated based current estimate of object image $f_Z^{(k)}$, and * represents convolution. Similar approach can be taken to compute the back-projection step. It is known that convolution is computationally more efficient than matrix multiplication using FFT algorithms. This idea can be extended to voxel sizes as a fraction of collimator pitch, where a multiple of X×Y convolutions of psf patterns and corresponding sub-images can be used. For example, if a voxel size is half of collimator pitch, 4 (2×2) times of 25 convolutions (i.e., a total of 100 convolutions) of psf patterns and corresponding sub-images can be used. This approach may bring higher accuracy with increased computational complexity.

Eq. (7) also indicates that if object image is organized in slices parallel to collimator surface denoted by distance Z, then the projection pattern $psf_{m,z}$ is the same for different angle $\alpha$. This further simplifies the algorithm.

One way is to implement Eq. (5) for each angle independently, taking $\alpha$ out of the summation; then take summation of estimate $f_{z(j)}$ along distance Z to obtain a secondary projection at that angle, $p'_\alpha$. Since the projection geometry to derive $p'_\alpha$ from object image f is similar to parallel hole collimation, algorithms for parallel hole collimation image reconstruction can be used to reconstruct f from $p'_\alpha$, such as filtered back-projection (FBP), algebraic reconstruction technique (ART), and OSEM methods.

An alternative is to convert $f_Z$ to $f_{\alpha,z}$ at the beginning of each iteration through interpolation, where $f_{\alpha,z}$ consists of slices (marked by Z) parallel to collimator surface at that angle. Then projection-back-projection steps can be executed before applying interpolation to convert the back-projected ratio, $q_{\alpha,z}$, given by $$q_{\alpha,Z} = \sum_i \frac{p(i,\alpha)K\alpha(i,j)}{\sum_{j,Z} K\alpha(i,j) f_{\alpha,Z}^{(k)}(j)}, \quad (8)$$

to original grid in f, and then calculate the updating ratio for $f_Z$.

Figures 8A, 8B, 8C:
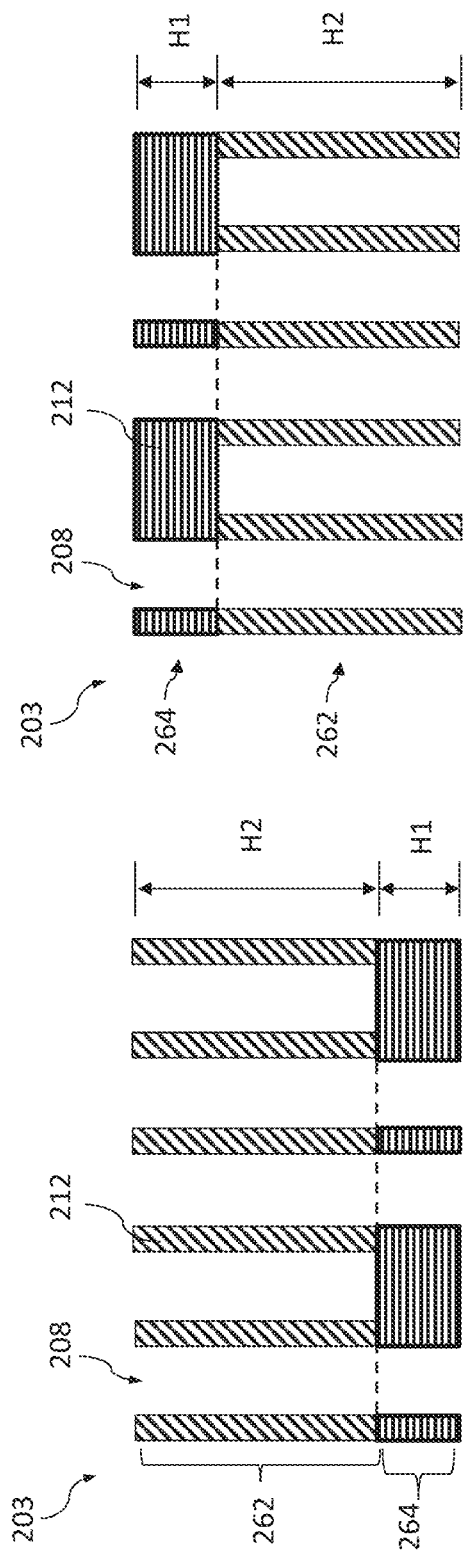

Referring back to FIG. 4, regarding the collimator 203, the height H of an aperture (i.e., the thickness of the collimator 203) is sometimes much larger than its opening width or diameter W. For example, an aperture width W may be less than 2 mm, while an aperture height H may be greater than 20 mm. However, for closed apertures, the apertures do not need to be fully filled, but rather to be filled with enough thickness to block radiation to pass through that hole. For example, when a radioisotope Tc-99m is used for material of septa, lead of 3 mm thickness may block more than 99% of incident radiation at 140 keV gamma rays. Hence the collimator may be fabricated in a light-weight form. Referring to FIGS. 8A and 8B, the collimator 203 is a collimator with open and closed holes and includes two sections. One section is similar to a parallel-hole collimator with uniformly distributed through-holes (also referred to as a parallel-hole section 262). The other section is substantially a thinner plate 264 (with thickness enough to substantially block radiation) with non-uniformly distributed through-holes, such as with less through-holes than those in the parallel-hole section 262 (e.g., approximately half of through-holes). The collimator 203 shown in FIGS. 8A and 8B is also referred to as multi-section collimator. The through-holes in the thin plate 264 are aligned with the through-holes in the parallel-hole section 262 to jointly define aperture pattern of the collimator 203, while other through-holes in the parallel-hole section 262 are blocked by the opaque material of the thin plate 264. Therefore, the through-holes in the thin plate 264 define the positions of the final apertures of the collimator 203. The thin plate 264 is also referred to as a patterned-aperture section 264. In some embodiments, all through-holes in the parallel-hole section 262 are substantially identical, while through-holes in the patterned-aperture section 264 may be different, even including closed ones. Further, the patterned-aperture section 264 may be moveable in some embodiments, such as operable to slide horizontally with respect to a surface of the parallel-hole section 262. Thus, multiple projection can be acquired at one angle by moving the patterned-aperture section 264 with respect to the parallel-hole section 262.

The patterned-aperture section 264 has a thickness H1 that is sufficiently thick to block targeted radiation. In various embodiments, a thickness H2 of the parallel-hole section 262 may be about 2 to about 10 times of the thickness H1 of the coded-aperture section 264. For example, an aperture length of 25 mm may be constructed with a parallel-hole section 262 having a thickness of 20 mm and a patterned-aperture section 264 having a thickness of 5 mm. In this way, the overall collimator weight can be significantly reduced compared with fully filled closed apertures. The patterned-aperture section 264 may be at one side of the parallel-hole section that faces the detector (FIG. 8A) or faces the target object (FIG. 8B), or even in the middle of two sub parallel-hole sections (e.g., sub parallel-hole sections 262-a and 262-b in FIG. 8C, where H2-a+H2-b=H2). In fact, the closed apertures only need a thin layer of heavy metal material to block radiation. This thin layer may even be broken up into multiple segments as needed. Hence this new design may start by fabricating regular parallel through-holes, then a thin layer may be placed anywhere inside the open though-holes to make closed apertures.

Although apertures illustrated in FIGS. 8A-8C have the same cross-section and opening width, many different designs exist to allow for different aperture profiles. For example, the light weight design can also be applied to collimators having apertures with the same pitch, but with different aperture size and septa. Some of such examples are illustrated in FIGS. 9A-9C. In FIG. 9A, the collimator 203 has some apertures with a diameter (or width) W and some apertures with a smaller diameter (or width) W'. Instead of using septa of constant width throughout the thickness of the collimator 203 for sidewalls of the narrower apertures, septa may have thicker portions merely at lateral ends. The thicknesses H1-a and H1-b at lateral ends are sufficient to block targeted radiation and maintain the same smaller acceptance angle Θ of what a narrower aperture designed to have. The spirit of the multi-part design above with reference to FIGS. 8A-8C can also be applied to the example collimator in FIG. 9A. FIG. 9B illustrates such a collimator 203 with one parallel-hole section 262 and two patterned aperture sections 264-a/264-b that define aperture sizes. In some cases, only one of 264-a/264-b is needed to adjust the acceptance angle Θ. Also, the apertures may have different shapes, both in cross-section and vertical section. The apertures may have different orientations in some embodiments. The patterned-aperture sections 264-a/264-b may define aperture sizes together with open and closed apertures patterns, such as shown in FIG. 9C. Referring to FIGS. 8A-9C collectively, one parallel-hole section 262 may be paired with different patterned-aperture sections 264a and/or 264b to create different collimators configurations. Therefore, multi-section collimators according to the present disclosure also provides a low-cost solution besides achieving light-weight designs. Notably, FIGS. 8A-C and 9A-C depict embodiments where adjacent sections of the multi-section collimator are in physical contact with each other. In alternative embodiment, the adjacent sections are tightly coupled to each other (to prevent photons from entering through one hole but exiting from another) without in physical contact as long as the collimator performance is assured.

Reference is now made to FIG. 10A. Unlike the exemplary collimators illustrated in FIGS. 8A-9C in which the parallel-hole section 262 and the patterned-aperture section 264 are attached to each other, the exemplary collimators as shown in FIG. 10A has the parallel-hole section 262 spaced from the patterned-aperture section 264. Further, the pattern-aperture section 264 may be tightly coupled to the detector 204. In the illustrated embodiment, a sensing pixel 214 of the detector 204 has a corresponding aperture in the patterned-aperture section 264 to receive illumination from the parallel holes further above in the parallel-hole section 262. The apertures in the patterned-aperture section 264 intentionally differ in sizes, resulting in different numbers of parallel holes in the parallel-hole section 262 that the pixels 214 can be illuminated. For example, a sensing pixel 214a has a larger corresponding aperture in the patterned-aperture section 264 than a neighboring sensing pixel 214b. As a result, the sensing pixel 214a can be illuminated by multiple parallel-holes in the parallel-hole section 262 bounded between the lines C1 and C2 intersecting the bottom surface of the parallel-hole section 262. As a comparison, due to a smaller corresponding aperture in the patterned-aperture section 264, the pixel 214b can only be illuminated by a single parallel hole that is directly above in the parallel-hole section 262 bounded by the lines D1 and D2 intersecting the bottom surface of the parallel-hole section 262. The number of parallel holes in the parallel-hole section 262 that can illuminate the same sensing pixel 214 depends on the acceptance angle of the corresponding aperture in the patterned-aperture section 264. The number of parallel holes in the parallel-hole section 262 that can illuminate the same sensing pixel 214 also depends on the distance H3 between the parallel-hole section 262 and the patterned-aperture section 264. The distance H3 is selected based on a need of the system performance. A general rule is to have a distance H3 allowing some of the pixels 214 of the detector 204 to be illuminated by at least two or more of the parallel holes 208 above. Notably, in an alternative embodiment as shown in FIG. 10B, it may be the parallel-hole section 262 that is tightly coupled to the detector 204, while the patterned-aperture section 264 is spaced apart from the parallel-hole section 262.

The design presented in this invention can be adapted to other variations with large number of long, narrow holes such as converging or diverging holes collimators, modified with the two features presented earlier.

Referring back to FIGS. 1A-1C, the radiation-based imaging system 100 may employ at least two different sets of coupled collimator and detector. In one of such embodiments, one set is with the SFI (spread-field imaging) collimator 203 (e.g., as shown in FIG. 4, 6A-C, 8A-C, 9A-C, or 10A-B) that is spaced from the coupled detector and the other with parallel-hole collimator 202 (e.g., as shown in FIG. 3) that is attached to the coupled detector. Usually in this configuration, the aperture opening (and/or acceptance angle) in the parallel-hole collimator 202 is smaller than the ones in the SFI collimator 203. As shown in Eq. (1), parallel-hole collimator generally offers good resolution at close range (small Z) because of smaller aperture opening, but its imaging resolution degrades quickly as the target object moves farther away from the collimator. In contrast, the SFI collimator 203 offers superior imaging resolution when the target object is farther away from the collimator. During a multi-angle image acquisition, the two sets of coupled collimator and detector module rotate around a target object to acquire images (projections). Naturally a certain part of the target object is close to one collimator at some angles and farther away at the opposite angle except for parts near the center of rotation (COR). By combining these two collimators, one may assign more weights to updating factors estimated from the parallel-hole collimator 202 projections for locations closer to the parallel-hole collimator 202, while more weights to updating factors estimated from the SFI collimator 203 projections for locations farther away from the parallel-hole collimator 202. State differently, the weighing between estimations of the two sets of coupled collimator and detector modules is distance-dependent. Another advantage of this configuration is that a quick estimate of object image can be obtained by reconstruction using the parallel hole projection alone and it can be used as initial estimate for the iterative reconstruction using projections from both collimators. There are several methods of choice to reconstruct multi-angle parallel hole projections, such as filtered back-projection (FBP), algebraic reconstruction technique (ART), and ordered subset expectation and maximization (OSEM). And the step may be carried out to reconstruct image at lower resolution (by applying low-pass filtering (LPF) on the projections, and/or reconstructed for larger pixels) to alleviate the lower counts due to the fact that parallel hole collimator projections here account for only half of angles of acquisition compared to conventional scan with dual camera both with parallel hole collimators. In another embodiment, the system employs at least two sets of coupled collimator and detector modules that both include an SFI collimator 203 (e.g., as shown in FIG. 4, 6A-C, 8A-C, 9A-C, or 10A-B) spaced from the coupled detector. But the long narrow through holes in the two collimators are with different acceptance angles. For example, the largest acceptance angle of one SFI collimator 203 is at least twice of the other SFI collimator 203, such as one for 100 and one for 5°. In another embodiment, the system employs at least two sets of coupled collimator and detector modules, at least one detector is coupled with an SFI collimator 203 (e.g., as shown in FIG. 4, 6A-C, 8A-C, 9A-C, or 10A-B) with long narrow holes (small acceptance angle) that is spaced from the coupled detector and another coupled with a multiple pinhole collimator, including coded aperture collimator where the largest aperture acceptance angle is substantially larger than those of the SFI collimator 203, such as more than 20°.

Referring to FIG. 1B, if the radiation-based imaging system 100 employs two identical sets of coupled collimator and detector in opposing positions, each set of coupled collimator and detector may only need to rotate half circle at equal sweeping steps. By combining data from the first and second half circles, the images from the full circle are acquired. For example, at a sweeping step of 3°, the first set may acquire images at angles 0°, 3°, 6°, . . . , 177° in sequence; the second set may acquire images at angles 180°, 183°, 186°, . . . , 357° in sequence. If the radiation-based imaging system 100 employs two different sets of coupled collimator and detector, since each set "sees" differently, each set needs to rotate a full circle. To maintain the same operating time, each set may sweep the full circle at twice the sweeping steps. For example, at a sweeping step of 6°, the first set may acquire images at angles 0°, 6°, 12°, . . . , 180°, 186°, . . . , 354° in sequence; the second set may acquire images at angles 180°, 186°, 192°, . . . , 354°, 0°, . . . , 174° in sequence. For each given angle swept by the system, two images will be acquired, one from the first set and another from the second set. State differently, although the two sets "see" differently, but each set repeats acquiring image from the same angle the other set has acquired from. As a comparison, referring to FIG. 1C, the two different sets of coupled collimator and detector are not exactly opposite but offset by half of the sweeping step. For example, if the sweeping step is 6°, the directions 154A and 154B in which the two sets point towards may form an angle T that is about 3°. Having an offset between the directions the two sets are pointing towards allows the system 100 to acquire each image from a different angle. For example, at a sweeping step of 6° and an offset of 3°, the first set may acquire images at angles 0°, 6°, 12°, . . . , 180°, 186°, . . . , 354° in sequence; the second set may acquire images at angles 183°, 189°, 195°, . . . , 357°, 3°, . . . , 177° in sequence.

Reference is now made to FIGS. 11A and 11B. In a radiation-based imaging system, the performance is optimized when apertures of a collimator are aligned with sensing pixels of a detector. FIG. 11A illustrates a top view in the X-Y plane of a portion of an exemplary SFI collimator 203 (a basic pattern as shown in FIG. 6B) superimposed on a detector 204. FIG. 11B illustrates a schematic cross-sectional view in the X-Z plane of a portion of the collimator 203 and the detector 204 along the A-A cut in FIG. 11A. The detector 204 as illustrated in FIGS. 10A and 10B includes an array of discrete sensing pixels 214. The discrete sensing pixels 214 may be based on CZT or SiPM structures. Typically, the sensing pixels 214 are arranged in a grid network (also referred to as the pixel grid) formed in rows and columns, such as the rows i=1, 2, 3, . . . and columns j=1, 2, 3, . . . in the illustrated embodiment. Any sensing pixel 214 located at a position (x, y) in the X-Y plane can be represented by an index (i, j) (i and j are integers) in the grid network and has a corresponding aperture (or a closed aperture in a coded pattern or a septum) in the grid network of the collimator 203 (also referred to as the aperture grid). Since the sensing pixels 214 in FIGS. 11A and 11B are discrete and physically distinctive from each other, to achieve alignment between a detector and a collimator is straightforward, that is to position the sensing pixels 214 directly under the corresponding apertures 208 of the collimator 203 such that the pixel grid and the aperture grid overlap.

Figures 12A, 12B:
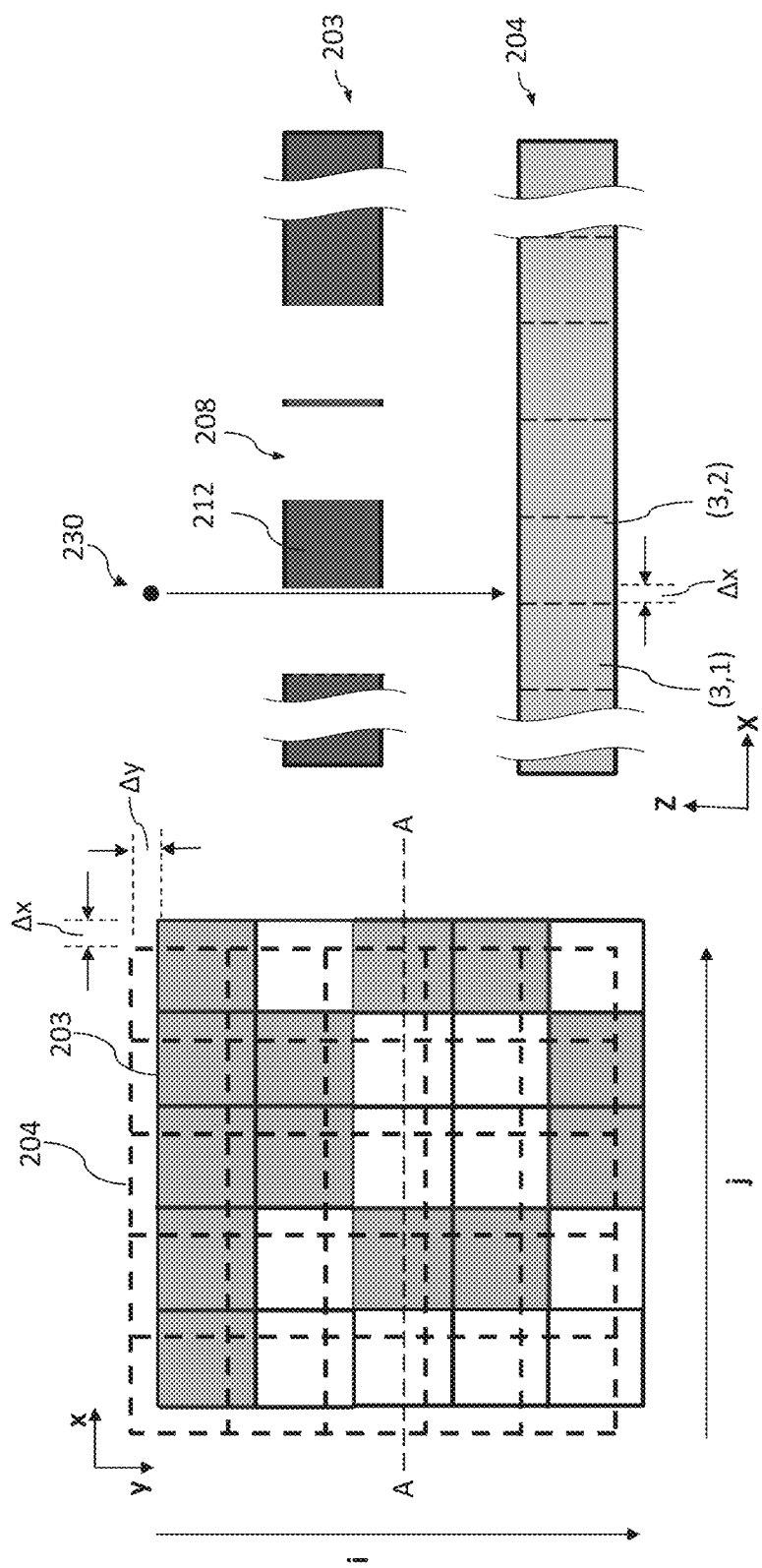

Reference is now made to FIGS. 12A and 12B. As discussed above in association with FIGS. 3 and 4, in some embodiments, sensing pixels of a detector are not physically distinctive from each other and are mere results of digitization of a continuous detector surface, as in the case of most PMT-based detector systems. FIG. 12A illustrates a top view in the X-Y plane of a portion of an exemplary SFI collimator 203 (a basic pattern as shown in FIG. 6B) superimposed on such a detector 204. FIG. 12B illustrates a schematic cross-sectional view in the X-Z plane of a portion of the collimator 203 and the detector 204 along the A-A cut in FIG. 12A. The detector surface is digitized as a pixel grid that is the same as the corresponding aperture grid of the collimator 203, i.e., of the same interspacing between grid points. In other words, each pixel grid unit on the detector surface has a corresponding aperture (or a closed aperture in a coded pattern or a septum) in the collimator 203, which is the nearest. Each pixel grid unit on the detector surface is also referred to as a pixel of the detector. The pixels of the detector are arranged in a grid network formed in rows and columns, such as the rows i=1, 2, 3, . . . and columns j=1, 2, 3, . . . and can be label as pixels (i, j) (i and j are integers). Ideally, under a perfect alignment, the pixel grid of the detector and the aperture grid of the collimator should overlap. However, as shown in FIGS. 12A and 12B, quite often a misalignment may occur between the pixel grid and the aperture grid, such as during apparatus assembly, resulting in misalignment in X-direction (denoted as Δx) and/or in Y-direction (denoted as Δy). The misalignment introduces degradation to the system. For example, as illustrated in FIG. 12B, an incident photon 230 traveling through an aperture of the collimator 203, which is supposed to be recorded as an event (e.g., a count) occurred at pixel (3, 1) under perfect alignment, would be instead recorded as an event occurred at pixel (3,2), therefore decreasing the contrast of aperture pattern in the recorded signal.

Figure 13:
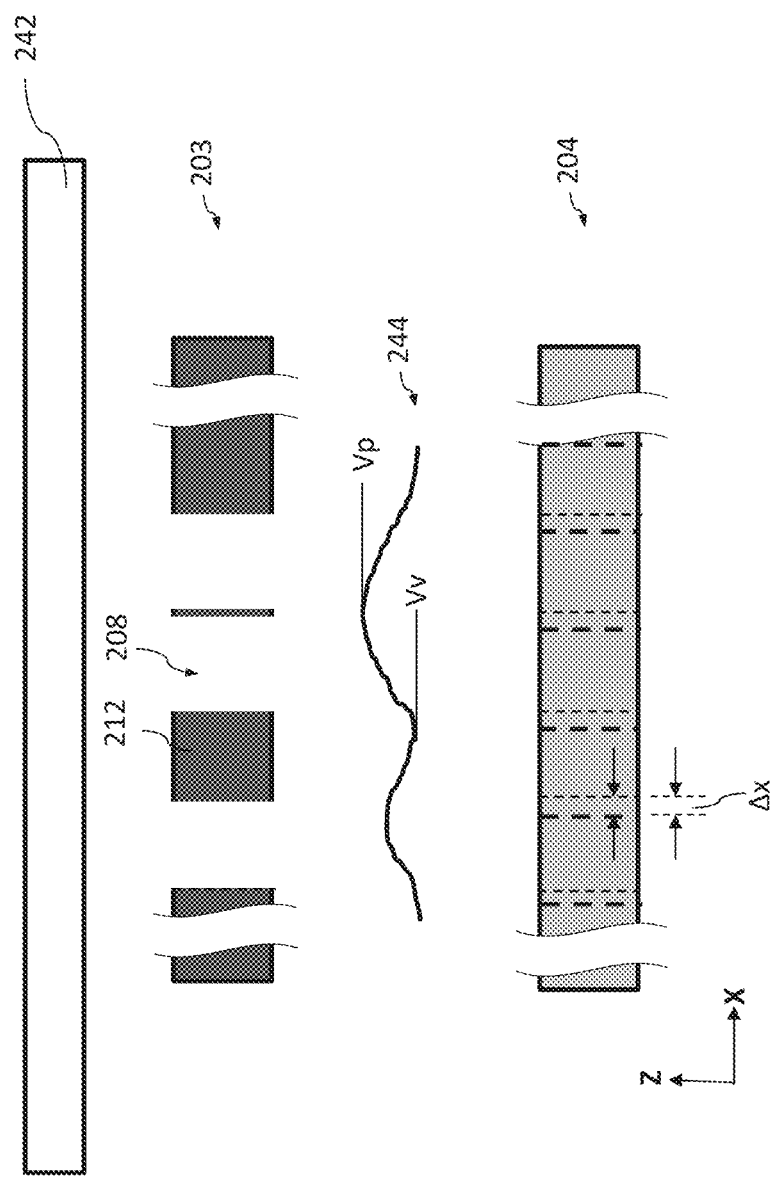

Taking a detector system based on photomultiplier tubes (PMT) as an example, where detector systems based on other structures are similar, briefly, the PMT functions by converting incident photons into photo-electrons at the photocathode. These electrons produce a large number of secondary electrons from a series of charged cathodes, generating a measurable current pulse at the anode. Based on these measurable current pulses in neighboring PMTs, a position (x, y) in the continuous X-Y plane can be determined as where the photon incident event occurs. Based on a mapping between the continuous X-Y plane and the (i, j) indices, an event occurred at the position (x, y) is subsequently digitized as an event occurred in pixel (i, j). However, as discussed above, due to misalignment relying on an initial mapping between the continuous X-Y plane and the (i, j) indices may introduce performance degradation. Image contrast provides a way of tuning to offset misalignments. In order for an image to be perceivable by the human eye and mind, the array of pixels of the acquired image must display contrast. Something about the specimen must produce changes in the signal intensity recorded at different pixels. At its simplest, transmission contrast may be due to structures that are partially or fully opaque, such as the apertures and closed apertures (or septa) of a collimator. The amount of contrast present in the image determines the accuracy with which it is critical to adjust the misalignment. A setup to offset the misalignment by algorithm without physically moving a collimator is illustrated in FIG. 13. In FIG. 13, a flood source 242, such as a Co-57 or Tc-99m rectangular flood source, provides a uniform field of radiation above the collimator 203. The flood source 242 can be positioned tightly coupled to the collimator 203, that is being less than half of a thickness of the collimator including the instance where the collimator 203 and the flood source 242 are in physical contact. Under the illumination of the flood source 242, the acquired image from the detector 204 is an image of the flood source 242 shadowed by the collimator 203. Due to the uniform radiation, the contrast in the acquired image is due to the transparent and opaque features of the collimator 203. In other words, the pixels underneath closed apertures (or septa) or small apertures yields weaker image signal intensity compared to the pixels underneath open or large apertures.

Contrast can be defined as a measure of the variation (e.g., a ratio or an absolute difference) of image single intensity between peak and valley. As an example, a signal intensity line 244 in FIG. 13 illustrates signal intensities $V_p$ and $V_v$ corresponding to a peak and a valley. One way to maximize contrast is to maximize the ratio of $V_p/V_v$ or to maximize the difference of $|V_p-V_v|/V_p$. When the contrast is maximized, the alignment between the collimator and the detector is considered as being achieved.

Since the detector surface is digitized into a pixel grid, offsetting the misalignment in other words, maximizing contrast—can be achieved by an algorithm without a need to physically move the collimator. In an exemplary method, each signal emerging from the detector surface (e.g., current pulses from PMT if in a PMT-based detector system) is recorded as an event with coordination (x, y). Thus, each entry in the data list (also referred to as list mode) is an attribute vector containing information about a single detected photon. For example, a stream of events may be labeled as $(x_n, y_n)$ (n=1, 2, 3, . . . ), where each pair represents the X- and Y-coordinates of the $n^{th}$ event detected. Based on a mapping between the continuous X-Y plane and the discrete (i, j) indices, the total counts reported in a pixel (i, j), denoted as C(i, j)), can be expressed as $$C(i,j)=\Sigma_{n=1}^{N}\delta(D(x_n,y_n)-(i,j)) \quad (9)$$

where D is the digitization function that maps an event occurred at (x, y) to a corresponding pixel (i, j), and $\delta$ function gives 1 if $D(x_n, y_n)$ is equal to (i, j), and 0 otherwise. Further, an energy window may be optionally applied to filter the events such that only when an event occurred within the energy window will be counted. By definition, C(i, j) is the image signal intensity at pixel (i, j), representing the number of events that are recorded in the area covered by pixel (i, j), which is defined by the digitization function D. The signal intensities at peak and valley, $V_p$ and $V_v$, can be identified from the set of C(i, j) (i=1, 2, 3, . . . ; j=1, 2, 3, . . . ) and an initial contrast ($V_p/V_v$ or $|V_p-V_v|/V_p$) can be calculated.

Next, an offset pair ($\delta$x, $\delta$y) is introduced in the digitization function to "offset" the pixel grid and recalculate C(i, j). Accordingly, C(i, j) can be expressed as $$C(i,j)=\Sigma_{n=1}^{N}\delta(D(x_n+\delta x,y_n+\delta y)-(i,j)) \quad (10)$$

where the introduction of ($\delta$x, $\delta$y) is equivalent to move the pixel grid in a distance of $\delta$x in the X-direction and a distance of $\delta$y in the Y-direction. As a result, an event occurred at a position (x, y) that would otherwise be recorded under pixel (i, j) may be regarded as equivalently have occurred at a position (x+$\delta$x, y+$\delta$y) and correspondingly recorded under a neighboring pixel (i', j'). The C(i, j) curve will thus be different and an updated contrast ($V_p/V_v$ or $|V_p-V_v|/V_p$) is calculated. The optimal ($\delta$x, $\delta$y) can be found to maximize the peak/valley contrast by a optimization method such as steepest decent, conjugate gradient, etc. An alternative is to create a series of offset pairs ($\delta$x, $\delta$y) at a small step. By sweeping the series of offset pairs ($\delta$x, $\delta$y), one offset pair ($\delta$x, $\delta$y) with the maximum contrast can be selected as the right offset amount to counter the misalignment, such as by regenerating the pixel grid. This offset pair ($\delta$x, $\delta$y) is termed selected offset pair or selected offset. Alternatively, the selected offset pair ($\delta$x, $\delta$y) can be applied to offset the origin ($x_0$, $y_0$) of the X-Y plane to shift the whole pixel grid (a special instance of regenerating the pixel grid). Ideally, the selected pair of ($\delta$x, $\delta$y) substantially equals the misalignment ($\Delta$x, $\Delta$y) but also depends on the sweeping steps used in generating the series of offset pairs ($\delta$x, $\delta$y). In various embodiments, the series of offset pairs ($\delta$x, $\delta$y) can be generated from equally dividing pixel pitches $P_x$ (pitch in the X-direction) and $P_y$ (pitch in the Y-direction), respectively. For example, for pixel pitches of 2.0 mm in both X- and Y-directions, the set of offset pairs ($\delta$x, $\delta$y) can be a sweeping with a step of 0.2 um starting from 0 with $\delta x<P_x$ and $\delta y<P_y$, that is a set of {(0, 0), (0.2 mm, 0), (0.4 mm, 0) . . . (2.0 mm, 1.8 mm), (2.0 mm, 2.0 mm)}. Other ways to generate the set of offset pairs ($\delta$x, $\delta$y) are possible, such as by bubble sort algorithm, bucket sort algorithm, insertion sort algorithm, or other suitable algorithms.

Instead of sweeping $\delta$x and $\delta$y together, alternatively, the method may sweep in the X-direction alone (by fixing a $\delta$y) to get an optimized offset $\delta$x in the X-direction first, then sweep in the Y-direction alone (by using the optimized $\delta$x) to get an optimized offset $\delta$y in the Y-direction subsequently. Or, similarly, the method may sweep in the Y-direction first then in the X-direction. Further, instead of picking $V_p$ and $V_v$ two dimensionally from the whole pixel grid to calculate contrast, the method may pick a row (by fixing i in the set of C(i, j), such as the signal intensity line 244 in FIG. 13) and sweep ($\delta$x, $\delta$y) to get a maximized contrast in the row and apply the selected offset pair ($\delta$x, $\delta$y) to whole pixel grid. Or, similarly, the method may pick a column (by fixing j in the set of C(i, j) and sweep ($\delta$x, $\delta$y) to get the maximized contrast in the column and apply the offset pair ($\delta$x, $\delta$y) to the whole pixel grid.

It is worth noting that different hole patterns may require different optimization approaches. In some patterns the maximum or minimum values of a descriptor (e.g., contrast, signal intensity at peak, or signal intensity at valley) of the recorded signal intensities may be used for maximization/minimization, such as a maximized contrast, a maximized peak value, or a minimized valley value. When repetitive hole patterns are used, corresponding pixels (corresponding to the same hole in the basic pattern) may be added together to reduce the randomness (i.e., quantum noise) in the pixel values. Also, in some embodiments when certain hole pattern is used, the selected offset pair ($\delta$x, $\delta$y) from the optimization routine, may be at a fixed offset away from the actual optimum offset, and that fixed offset is determined by the hole pattern. For example, in some hole patterns, the maximum pixel value in a flood source image is located in the middle of neighboring 2×2 open holes. In that case, the fixed offset is half a hole pitch, and the actual optimum offset used to align pixels to holes would be corrected by the fixed offset. In other words, after a selected offset pair ($\delta$x, $\delta$y) is found, a further step may be optionally performed to add or subtract a fixed offset to or from the selected offset pair ($\delta$x, $\delta$y) in getting an actual optimum offset to use for misalignment adjustment.

Although not intended to be limiting, one or more embodiments of the present disclosure provide many benefits for radiation-based imaging of a target object, such as a patient. For example, a collimator design with repetitive coded pattern that is spaced away from an associated detector provides superior imaging resolution without sacrificing signal sensitivity. Therefore, system performance is improved.

The foregoing outlines features of several embodiments so that those of ordinary skill in the art may better understand the aspects of the present disclosure. Those of ordinary skill in the art should appreciate that they may readily use the present disclosure as a basis for designing or modifying other processes and structures for carrying out the same purposes and/or achieving the same advantages of the embodiments introduced herein. Those of ordinary skill in the art should also realize that such equivalent constructions do not depart from the spirit and scope of the present disclosure, and that they may make various changes, substitutions, and alterations herein without departing from the spirit and scope of the present disclosure. Accordingly, it is appropriate that the appended claims be construed broadly and in a manner consistent with the present disclosure.

What is claimed is:

1. A method for image processing, comprising:
   obtaining a first image having M sections and each of the M sections having X rows and Y columns of pixels, wherein each of M, X, and Y is an integer greater than 0, and the X rows and Y columns of pixels in each of the M sections are indexed from 1 to (X×Y);
   deriving (X×Y) first sub-images from the first image, wherein each first sub-image has M sections, each section of each first sub-image has X rows and Y columns of pixels that are indexed from 1 to (X×Y), the (X×Y) first sub-images are indexed from 1 to (X×Y), wherein the i-th pixel of the j-th section of the i-th first sub-image has a pixel value equal to a pixel value of the i-th pixel of the j-th section of the first image and other pixels of the j-th section of the i-th first sub-image are set to 0, where i traverses from 1 to (X×Y) and j traverses from 1 to M;
   providing (X×Y) first projection patterns;
   for each of the (X×Y) first sub-images, calculating a first projection by performing convolution of the respective first sub-image with a corresponding one of the first projection patterns, thereby obtaining (X×Y) projected first sub-images; and
   summing up the (X×Y) projected first sub-images, thereby obtaining a projection of the first image.

2. The method of claim 1, wherein the first image is an object image at a first distance from a collimator having repetitive basic patterns, each basic pattern is a (X×Y) aperture pattern, and each of the (X×Y) first projection patterns is derived by projecting a point source at a plane located at the first distance from the collimator with the point source being directly above one of the apertures of the basic pattern.

3. The method of claim 2, wherein a size of the point source is same as a pitch of the collimator.

4. The method of claim 2, wherein a size of the point source is a fraction of a pitch of the collimator.

5. The method of claim 2, further comprising:
   providing a detector coupled with the collimator, wherein the collimator is spaced away from the detector, wherein each of the (X×Y) first projection patterns is derived by projecting the point source through the collimator onto the detector.

6. The method of claim 2, further comprising:
   obtaining a second image that is the object image at a second distance from the collimator, wherein the second distance is different from the first distance, the second image has M sections, each of the M sections has X rows and Y columns of pixels, and the X rows and Y columns of pixels in each of the M sections are indexed from 1 to (X×Y);
   deriving (X×Y) second sub-images from the second image, wherein each second sub-image has M sections, each section of each second sub-image has X rows and Y columns of pixels that are indexed from 1 to (X×Y), the (X×Y) second sub-images are indexed from 1 to (X×Y), wherein the i-th pixel of the j-th section of the i-th second sub-image has a pixel value equal to a pixel value of the i-th pixel of the j-th section of the second image and other pixels of the j-th section of the i-th second sub-image are set to 0, where i traverses from 1 to (X×Y) and j traverses from 1 to M;
   providing (X×Y) second projection patterns;
   for each of the (X×Y) second sub-images, calculating a second projection by performing convolution of the respective second sub-image with a corresponding one of the second projection patterns, thereby obtaining (X×Y) projected second sub-images;
   summing up the (X×Y) projected second sub-images, thereby obtaining a projection of the second image; and
   summing the projection of the first image and the projection of the second image.

7. The method of claim 1, further comprising:
   acquiring a projection of an object at an angle using an imaging system having a collimator and a detector, wherein the collimator has repetitive basic patterns wherein each basic pattern is a (X×Y) aperture pattern.

8. The method of claim 1, wherein the M sections are contiguous.

9. The method of claim 1, wherein at least two of the (X×Y) first projection patterns are different from each other.

10. The method of claim 1, wherein all of the (X×Y) first projection patterns are different from each other.

11. A method for image processing, comprising:
    obtaining an image, wherein the image is an object image at a distance from a collimator having repetitive basic patterns, each basic pattern is a (X×Y) aperture pattern, wherein the image has M sections and each of the M sections has X rows and Y columns of pixels, wherein each of M, X, and Y is an integer greater than 0, and the X rows and Y columns of pixels in each of the M sections are indexed from 1 to (X×Y);
    deriving (X×Y) sub-images from the image, wherein each sub-image has M sections and each section of each sub-image has X rows and Y columns of pixels, the (X×Y) sub-images are indexed from 1 to (X×Y), wherein for each j-th section of each i-th sub-image, the i-th pixel has a pixel value equal to a pixel value of the i-th pixel of the j-th section of the image and other pixels of the j-th section of the i-th sub-image are set to 0, where i traverses from 1 to (X×Y), and j traverses from 1 to M;
    providing (X×Y) projection patterns by projecting a point source at a plane located at the distance from the collimator with the point source being directly above one of the apertures of the basic pattern;
    for each of the (X×Y) sub-images, calculating a projection by performing convolution of the respective sub-image with a corresponding one of the projection patterns, thereby obtaining (X×Y) projected sub-images; and summing up the (X×Y) projected sub-images, thereby obtaining a projection of the image.

12. The method of claim 11, further comprising:
providing a detector coupled with the collimator, wherein each of the (X×Y) projection patterns is derived by projecting the point source through the collimator onto the detector.

13. The method of claim 11, wherein a size of the point source is same as a pitch of the collimator or is a fraction of the pitch of the collimator.

* * * * *